US008858602B2

(12) United States Patent
Weiner et al.

(10) Patent No.: US 8,858,602 B2
(45) Date of Patent: Oct. 14, 2014

(54) BONE DEFECT REPAIR DEVICE AND METHOD

(75) Inventors: Lon S. Weiner, Rumson, NJ (US); Stuart D. Katchis, Scarsdale, NY (US)

(73) Assignee: Nextremity Solutions, Inc., Red Bank, NJ (US)

( * ) Notice: Subject to any disclaimer, the term of this patent is extended or adjusted under 35 U.S.C. 154(b) by 71 days.

(21) Appl. No.: 13/364,240

(22) Filed: Feb. 1, 2012

(65) Prior Publication Data

US 2012/0303033 A1    Nov. 29, 2012

Related U.S. Application Data

(60) Provisional application No. 61/457,212, filed on Feb. 1, 2011.

(51) Int. Cl.
| | |
|---|---|
| *A61B 17/66* | (2006.01) |
| *A61B 17/15* | (2006.01) |
| *A61B 17/80* | (2006.01) |
| *A61B 17/17* | (2006.01) |
| *A61B 17/56* | (2006.01) |

(52) U.S. Cl.
CPC ....... *A61B 17/151* (2013.01); *A61B 2017/1775* (2013.01); *A61B 2017/565* (2013.01); *A61B 17/8061* (2013.01)
USPC .......................................... 606/282; 606/286

(58) Field of Classification Search
USPC ................................................. 606/282, 286
See application file for complete search history.

(56) References Cited

U.S. PATENT DOCUMENTS

| | | |
|---|---|---|
| 3,866,607 A | 2/1975 | Forsythe et al. |
| 4,409,973 A | 10/1983 | Neufeld |

(Continued)

FOREIGN PATENT DOCUMENTS

| | | |
|---|---|---|
| FR | 2764183 | 12/1998 |
| JP | 5245159 | 9/1993 |
| WO | WO 2007/025520 | 3/2007 |
| WO | WO 2007/126622 | 11/2007 |

OTHER PUBLICATIONS

Bosch et al., Hallux Valgus Correction by the Method of Bosch: A New Technique With a Seven-to-Ten-Year Follow-Up, from Foot and Ankle Clinics, The Hallux, ed. Andrea Cracchiolo, III, MD, Sep. 2000, pp. 485-498, vol. 5, No. 3.

(Continued)

*Primary Examiner* — Andrew Yang
*Assistant Examiner* — Olivia C Chang
(74) *Attorney, Agent, or Firm* — Heslin Rothenberg Farley & Mesiti P.C.

(57) ABSTRACT

In a method and system for corrective bunionectomy surgery of a bone, a saw template is positioned at a proximal portion of the bone. The saw template has a plurality of pin holes, for the insertion of pins. The saw template is replaced with a saw block placed over a portion of the plurality of pins. The bone is cut into first and second bone segments based on a position of the saw block. The saw block is removed. A corrective angle is applied to the second bone segment relative to the first bone segment. A mating plate compatible with the corrective angle is positioned over the plurality of pins to join the first bone segment and the second bone segment. A plurality of bone screws is screwed into the mating plate to secure the first bone segment and the second bone segment to form a corrective construct.

31 Claims, 26 Drawing Sheets

(56) References Cited

U.S. PATENT DOCUMENTS

| | | | |
|---|---|---|---|
| 4,509,511 | A | 4/1985 | Neufeld |
| 4,565,191 | A | 1/1986 | Slocum |
| 4,718,413 | A | 1/1988 | Johnson |
| 5,021,056 | A | 6/1991 | Hofmann et al. |
| 5,042,983 | A | 8/1991 | Rayhack |
| 5,112,334 | A | 5/1992 | Alchermes et al. |
| 5,423,827 | A | 6/1995 | Mumme et al. |
| 5,490,854 | A | 2/1996 | Fisher et al. |
| 5,540,695 | A | 7/1996 | Levy |
| 5,601,565 | A | 2/1997 | Huebner |
| 5,843,085 | A | 12/1998 | Graser |
| 5,935,128 | A | 8/1999 | Carter et al. |
| 6,190,390 | B1 | 2/2001 | McAllister |
| 6,391,031 | B1 | 5/2002 | Toomey |
| 6,547,793 | B1 | 4/2003 | McGuire |
| 6,964,664 | B2 | 11/2005 | Freid et al. |
| 7,018,383 | B2 | 3/2006 | McGuire |
| 8,177,820 | B2 | 5/2012 | Anapliotis et al. |
| 2002/0068942 | A1 | 6/2002 | Neubauer et al. |
| 2004/0127900 | A1 | 7/2004 | Konieczynski et al. |
| 2004/0193165 | A1 | 9/2004 | Orbay |
| 2005/0049594 | A1* | 3/2005 | Wack et al. .............. 606/69 |
| 2005/0273112 | A1 | 12/2005 | McNamara |
| 2006/0015102 | A1 | 1/2006 | Toullec et al. |
| 2006/0241608 | A1 | 10/2006 | Myerson et al. |
| 2006/0264961 | A1 | 11/2006 | Murray-Brown |
| 2007/0016205 | A1 | 1/2007 | Beutter et al. |
| 2007/0123880 | A1 | 5/2007 | Medoff |
| 2007/0173815 | A1 | 7/2007 | Murase |
| 2009/0157121 | A1 | 6/2009 | Harris et al. |
| 2009/0306723 | A1 | 12/2009 | Anapliotis et al. |
| 2010/0274293 | A1 | 10/2010 | Terrill et al. |

OTHER PUBLICATIONS

Coull et al., Operative decision making in hallux valgus, Current Orthopaedics, 2002, pp. 180-186, vol. 16.

Feldman, The Green-Waterman Procedure: Geometric Analysis and Preoperative Radiographic Template Technique, Journal of Foot Surgery, 1992, pp. 182-185, vol. 21, No. 2.

FR 2764183 published Dec. 11, 1998, abstract only in English, downloaded from espacenet.com, 1 page.

Gerbert et al., Youngwick-Austin Procedure: The Effect of Plantar Arm Orientation on Metatarsal Head Displacement, 2001, pp. 8-14, vol. 40, No. 1.

Hofstaetter et al., Biomechanical comparison of screws and plates for hallux valgus opening-wedge and ludloff osteotomies, Clinical Biomechanics, 2008, pp. 101-108, vol. 23.

Instrumentation Systems for Scoliosis Surgery, National Scoliosis Foundation, downloaded from the internet at http://www.scoliosis.org/resources/medicalupdates/instrumentationsystems.php on Jan. 17, 2008, 3 pages.

International Search Report and Written Opinion dated Jun. 4, 2012 in related International Application No. PCT/US2012/023552 filed Feb. 1, 2012, 8 pages.

Jones et al., Proximal Crescentric Metatarsal Osteotomy: The Effect of Saw Blade Orientation on First Ray Elevation, Foot and Ankle International, 2005, pp. 152-157, vol. 26, No. 2.

JP 5245159 published Sep. 24, 1993, abstract only in English, downloaded from espacenet.com, 2 pages.

Miller et al., A review of locking compression plate biomechanics and their advantages as internal fixators in fracture healing, Clinical Biomechanics, 2007, pp. 1049-1062 vol. 22.

Muhlbauer et al., Short-term Results of the modified Chevron osteotomy with soft-tissue release and guide-wire fixation A prospectives, Z Orthop, 2000, pp. 435-439, vol. 138, in German, abstract only in English.

Nyska et al., The Ludloff Metatarsal Osteotomy: Guidelines for Optimal Correction Based on a Geometric Analysis Conducted on a Sawbone Model, Foot and Ankle International, Jan. 2003, pp. 34-39, vol. 24, No. 1.

Reese et al., Reese Osteotomy Guide System, Journal of Foot Surgery, 1984, pp. 386-391, vol. 23, No. 5.

Roussignol et al., Use of new angle DM2AA for the therapeutic planning of the hallux valgus, 2006, vol. 92, No. S4, in French, abstract only in English.

Van Heerwaarden et al., Distal Medial Closed Wedge Varus Femur Osteotomy Stabilized With the TomoFix Plate Fixator, Oper Tech Orthop, 2007, pp. 12-21, vol. 17.

Woodle, Preoperative Planning for Hallux Valgus Bunion Surgery: Photonics Versus Templates, from Hallux Valgus and Allied Deformities, Clinics in Podiatric Medicine and Surgery, 1989, pp. 27-45, vol. 6, No. 1.

Zecchini et al., Template for the preoperative planning of halux valgus (undertoe), Foot and Ankle Surgery, 2001, pp. 53-56, vol. 7.

* cited by examiner

BONE DEFECT REPAIR DEVICE AND METHOD

CROSS-REFERENCE TO RELATED APPLICATIONS

The present application claims the benefit of U.S. Provisional Application Ser. No. 61/457,212 filed Feb. 1, 2011, which is incorporated herein by reference in its entirety.

TECHNICAL FIELD

The present invention relates to corrective bunionectomy surgery.

BACKGROUND OF THE INVENTION

Bunions are deformities of bones and the joint found on a person's foot, causing pain for any individual having them. A bunionectomy is a surgical procedure to remove painful bunions. Typically, bunionectomy surgery involves correction of the foot by reconstructing bones and joints. Recurrence of the bunion may occur if the metatarsal experiences a change in alignment after surgery. Thus, secure fixation of any cut metatarsal bone sections is important to ensure a successful bunionectomy procedure.

SUMMARY OF THE INVENTION

A method and system for corrective bunionectomy surgery of a bone is disclosed. A saw template is positioned at a proximal portion of the bone. The saw template has a plurality of pin holes. A plurality of pins is inserted into the plurality of pin holes of the saw template. The saw template is replaced with a saw block placed over a portion of the plurality of pins. The bone is cut into a first bone segment and a second bone segment based on a position of the saw block. The saw block is removed. A corrective angle is applied to the second bone segment relative to the first bone segment. A mating plate compatible with the corrective angle is positioned over the plurality of pins to join the first bone segment and the second bone segment. A plurality of bone screws is screwed into the mating plate to secure the first bone segment and the second bone segment to form a corrective construct.

In an embodiment, the bone is a first metatarsal bone.

In an embodiment, the plurality of pin holes comprises a first pin hole and a second pin hole on a first half of the saw template and a third pin hole and a fourth pin hole on a second half of the saw template, the first pin hole and the second pin hole oriented perpendicular to a long axis of the bone, and the third pin hole and the fourth pin hole oriented parallel to the long axis of the bone. The saw template is positioned at the proximal portion of the bone such that the first half of the saw template is at a first proximal portion of the bone and the second half of the saw template is at a second proximal portion of the bone. The saw template is positioned in parallel to the long axis of the bone.

In an embodiment, the plurality of pins are 1.5 mm K-wire pins.

In an embodiment, the saw template is replaced with a saw block by positioning the saw block over two of the plurality of pins adjacent to the proximal portion of the bone. The proximal portion of the bone connects to the metatarsal-medial cuneiform joint.

In an embodiment, the bone is cut into a first bone segment and a second bone segment through a saw slot of the saw block.

In an embodiment, the corrective angle is one of: 5 degrees, 10 degrees, and 15 degrees.

In an embodiment, the plurality of bone screws are 3.5 mm bone screws.

In an embodiment, a plurality of pilot holes is drilled into the first bone segment and the second bone segment based on corresponding guide holes of the mating plate. The mating plate comprises a first mating plate section that attaches to the first bone segment and a second mating plate section that attaches to the second bone segment. A plurality of bone screws is screwed into a plurality of pilot holes in the first bone segment based on corresponding guide holes in the first mating plate section. A compression bone screw is screwed into the second bone segment at a pilot hole corresponding to a compression screw guide hole at a proximal end of the second mating plate section to affect compression between the first bone segment and the second bone segment causing the second bone segment to move in a proximal direction towards the first bone segment. A plurality of bones screws are screwed into the second bone segment at any remaining pilot holes corresponding to guide holes in the second mating plate section.

In an embodiment, the plurality of pins are removed from the corrective construct.

A mating plate for joining a first bone segment and a second bone segment is disclosed. A proximal mating plate section comprises a plurality of pin holes for mating with a plurality of pins on the first bone segment, and a plurality of guide holes for receiving bone screws into the first bone segment. A distal mating plate section comprises a plurality of enlarged pin holes for mating with a plurality of pins on the second bone segment; a compression screw guide hole for receiving a compression bone screw into the second bone segment; and a plurality of guide holes for receiving bone screws into the second bone segment. Tightening of the compression bone screw causes the second bone segment to move in a proximal direction towards the first bone segment.

These and other advantages of the invention will be apparent to those of ordinary skill in the art by reference to the following Detailed Description and accompanying drawings/figures.

DETAILED DESCRIPTION

The present invention described herein provides a system and method for corrective bunionectomy surgery. The present invention facilitates easy to apply bone cuts and secure fixation of cut metatarsal bone sections. Proximal and distal bone screws on each side of the bone cut assist in securing the fixation of metatarsal bone sections. K-wire pins facilitate the positioning of a correction angle and maintenance of this angle. Elongated k-wire holes on a mating plate for fixating the cut metatarsal bone sections support bone compression, the elongated k-wire holes for receiving k-wire pins.

Provided herein is a system and method for carrying out corrective bunionectomy surgery. In the various embodiments described herein and corresponding with the Figures provided herewith, a corrective surgery method and system are described with respect to a metatarsal bone. A saw template is positioned on the bone and fixed in position with K-wire pins. The saw template is removed and the K-wire pins left in the bone. A saw block is placed over two of the K-wire pines and a saw cut is made guided by the saw block to cut the bone into two segments. A corrective angle is applied to one of the segments, and a mating plate is placed over the K-wire pins of the two segments. Bone screws are applied to the mating plate to recombine the two bone segments such that a bunion no longer protrudes.

Figure 1:
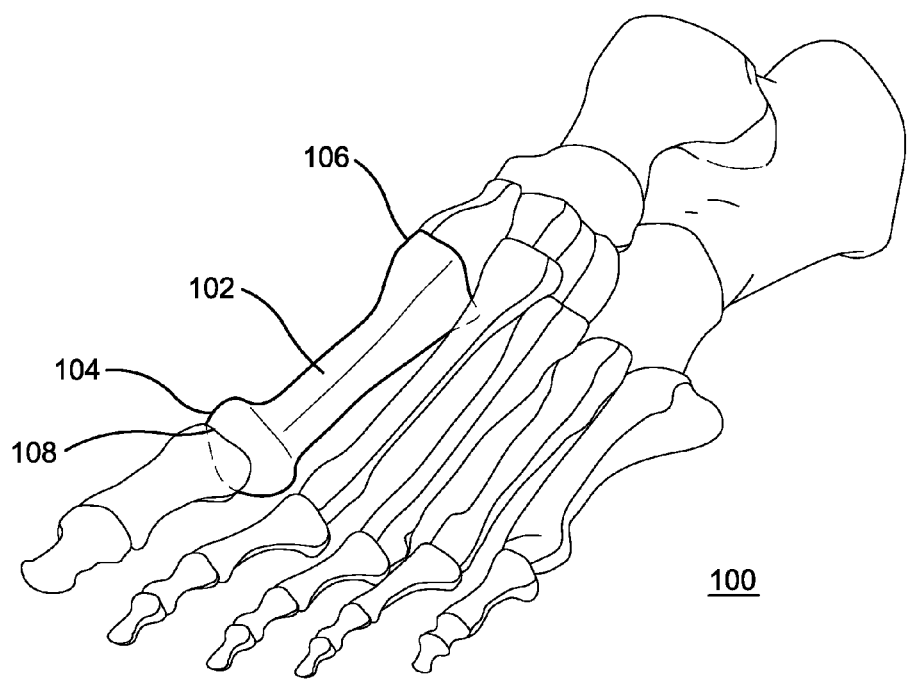
FIG. 1 illustrates a perspective view of an exemplary left foot bone structure, in accordance with an embodiment.

FIG. 1 illustrates a perspective view of an exemplary left foot bone structure, in accordance with an embodiment. Left foot bone structure 100 includes a first metatarsal bone 102, and a bunion 104 located at a distal end 108 of the first metatarsal bone 102. By way of illustration and description, the following paragraphs and corresponding figures describe a system and method for corrective bunionectomy surgery for the left foot. However, it is understood that the system and method may also be applied to the right foot bone structure in a similar fashion.

Figure 2:
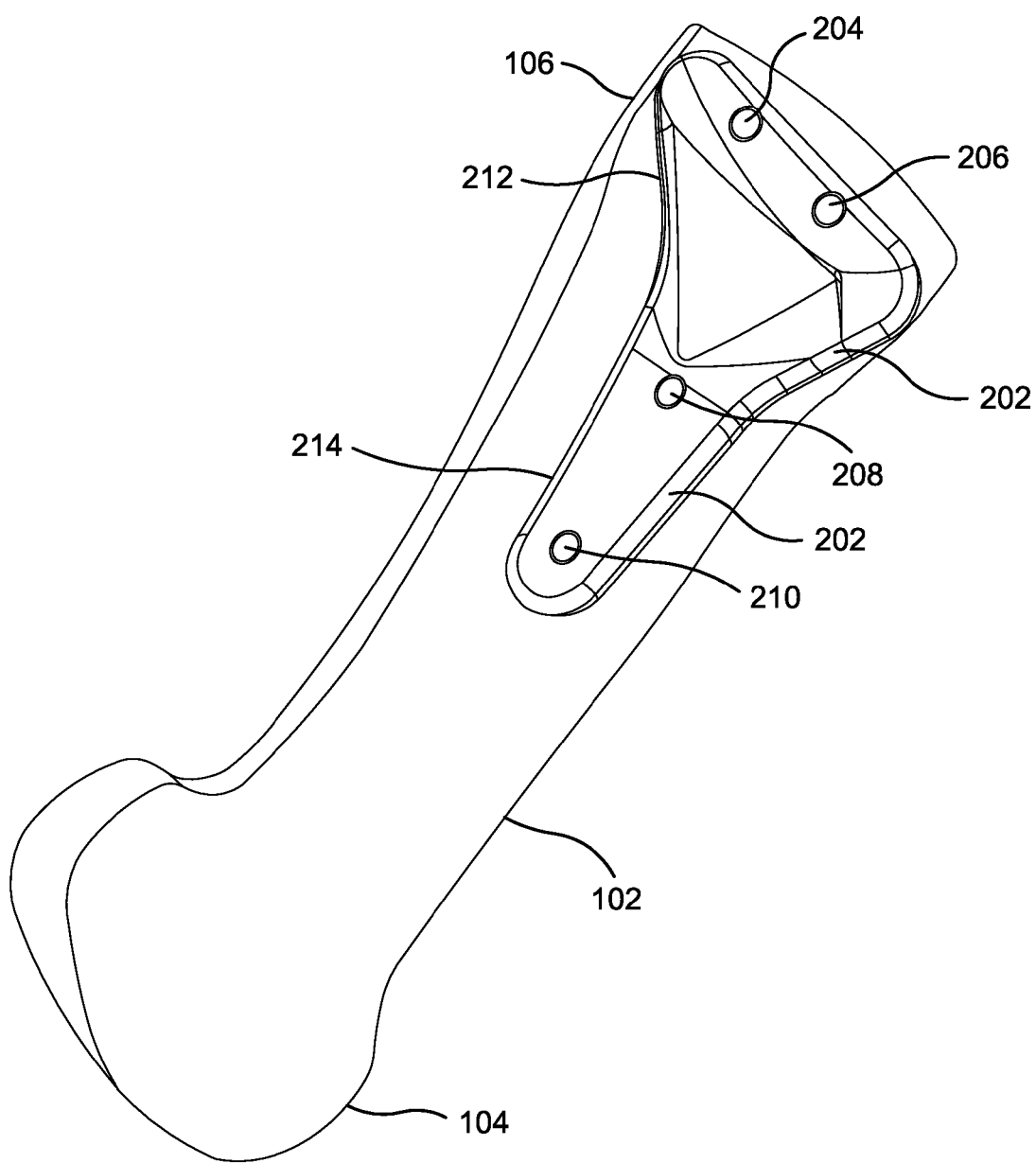
FIG. 2 illustrates a perspective view of an exemplary first metatarsal bone with saw template, in accordance with an embodiment.

FIG. 2 illustrates a perspective view of an exemplary first metatarsal bone with saw template, in accordance with an embodiment. Metatarsal bone 102 is shown after exposure of the bone during surgery. Saw template 202 is positioned at a proximal end 106 of metatarsal bone 102. Saw template 202 includes first, second, third, and fourth pin holes 204, 206, 208, and 210. First and second pin holes 204 and 206 at a proximal half 212 of saw template 202 are oriented perpendicular to a long axis of metatarsal bone 102. Third and fourth pin holes 208 and 210 at a distal half 214 of saw template 202 are oriented parallel to the long axis of metatarsal bone 102. Saw template 202 is positioned lengthwise in parallel with the long axis of metatarsal bone 102.

Figure 3:
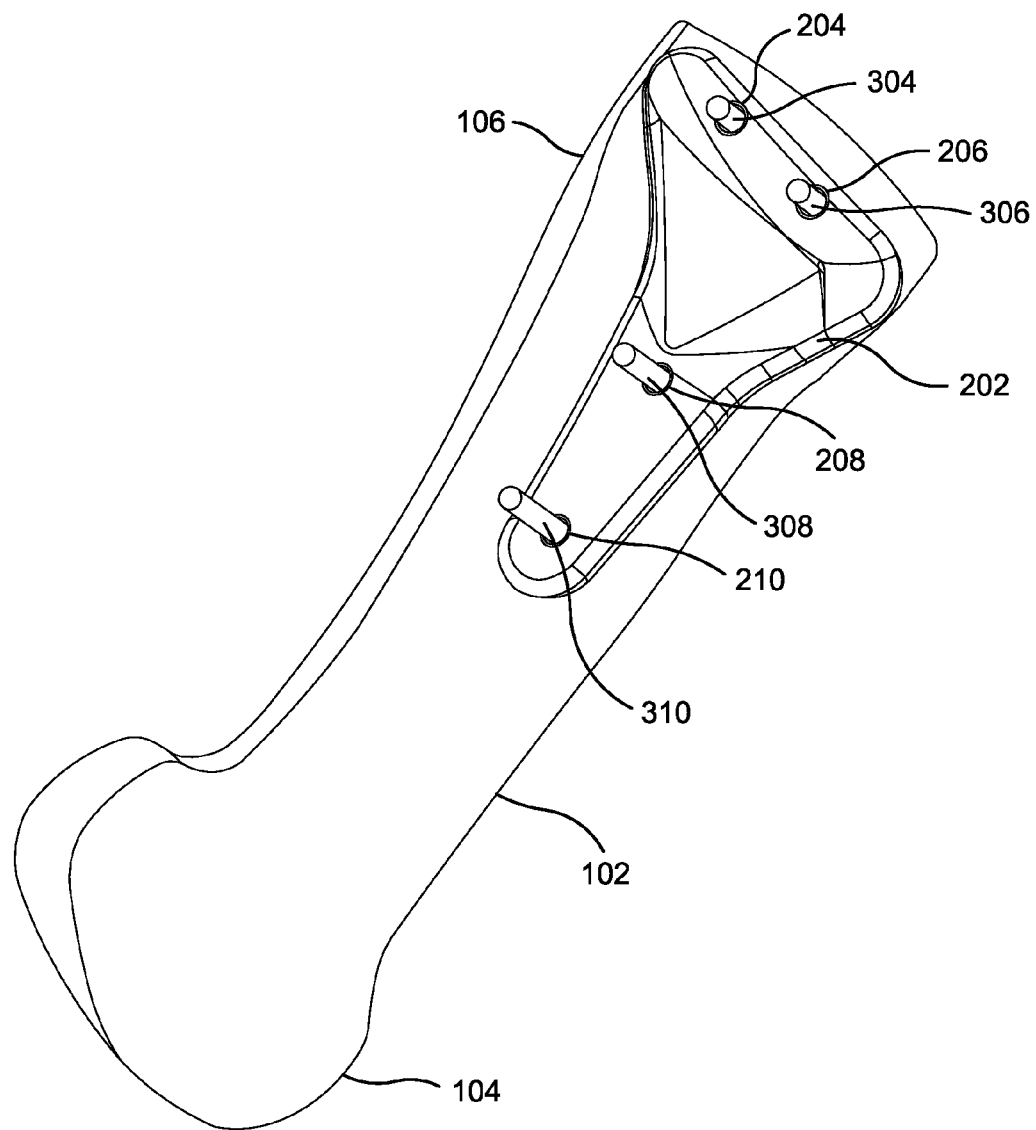
FIG. 3 illustrates a perspective view of the saw template on the metatarsal bone affixed with K-wire pins, in accordance with an embodiment.

FIG. 3 illustrates a perspective view of the saw template on the metatarsal bone affixed with K-wire pins, in accordance with an embodiment. First, second, third, and fourth pin holes 204, 206, 208, and 210 have been filled with four short 1.5 mm K-wire pins 304, 306, 308, and 310. Saw template 202 is fixed in a position according to K-wire pins 304, 306, 308, and 310. Saw template 202 serves as a template for insertion of the K-wire pins.

Figure 4:
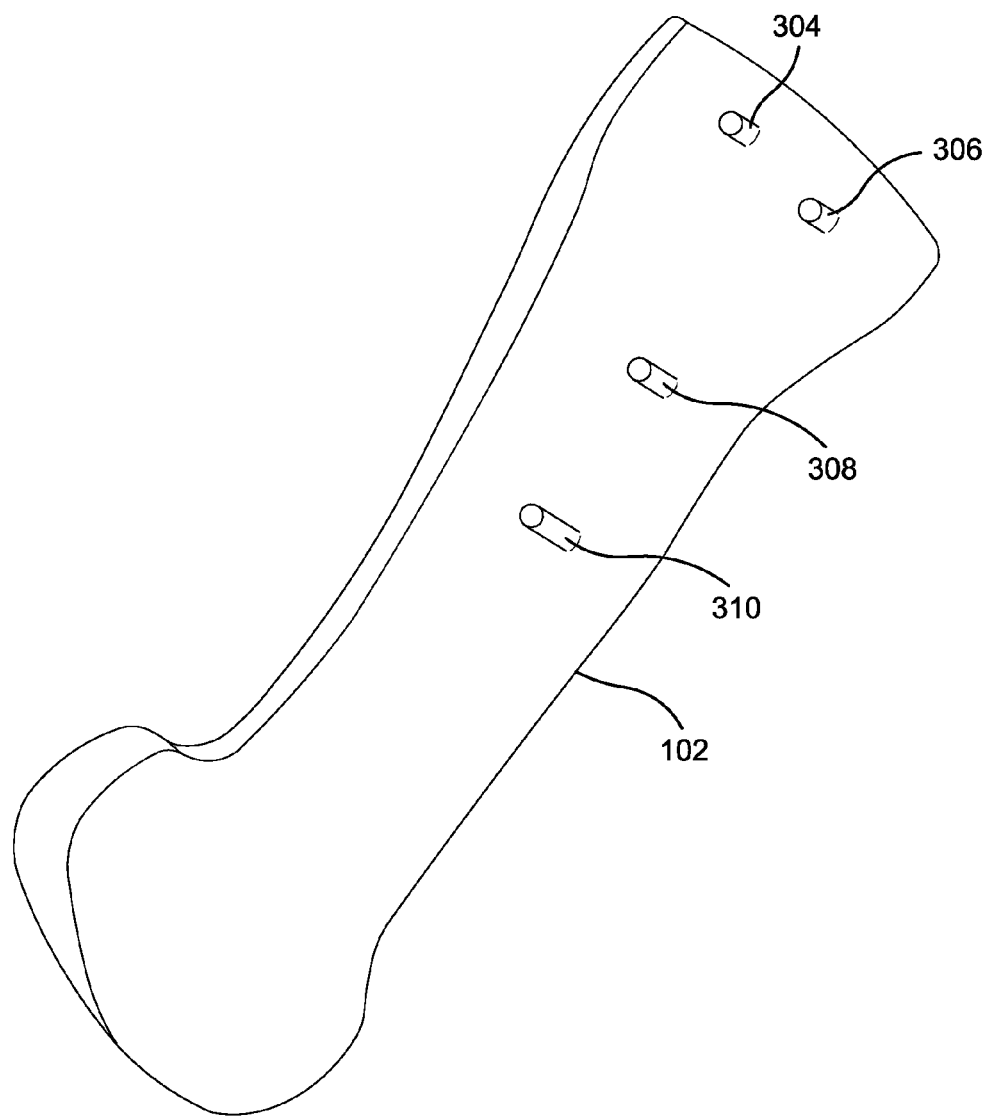
FIG. 4 illustrates a perspective view of the metatarsal bone with saw template removed, in accordance with an embodiment.

FIG. 4 illustrates a perspective view of the metatarsal bone with saw template removed, in accordance with an embodiment. Saw template 202 is removed after K-wire pins 304, 306, 308, and 310 are inserted. K-wire pins 304, 306, 308, and 310 are left in metatarsal bone 102.

Figure 5:
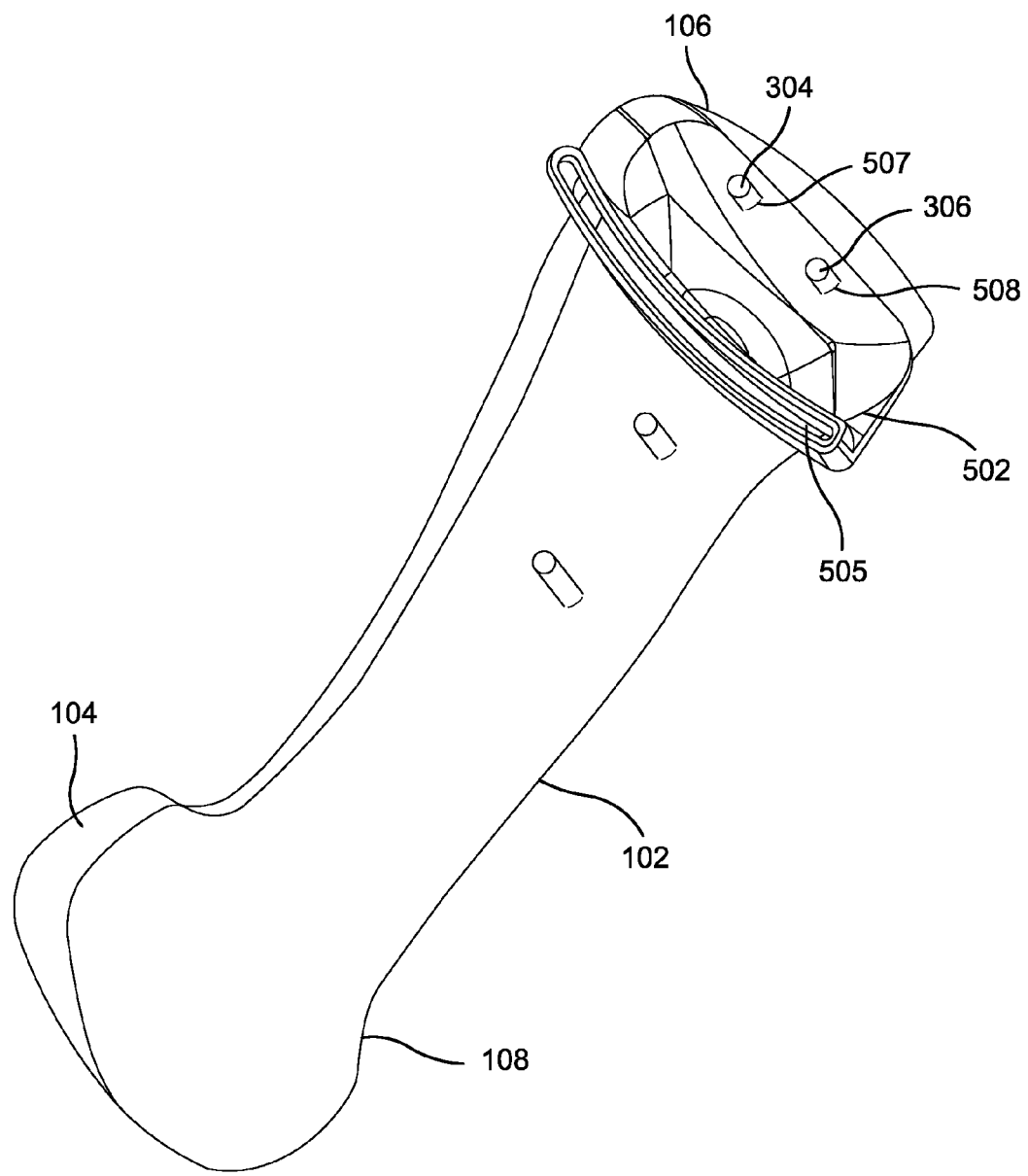
FIG. 5 illustrates a perspective view of a saw block placed on the metatarsal bone, in accordance with an embodiment.

FIG. 5 illustrates a perspective view of a saw block placed on the metatarsal bone, in accordance with an embodiment. Saw block 502, includes two pin holes 507 and 508, configured to mate with K-wire pins 304 and 306, is placed over K-wire pins 304 and 306 at the proximal end 106 of metatarsal bone 102. Proximal end 106 is also where the metatarsal-medial cuneiform joint is located. Saw block 502 includes a saw slot 505 which provides an opening thru which a saw may be inserted to cut along the saw slot 505. The cut according to saw slot 505 may be made with a powered cutting saw. After the cut is made into metatarsal bone 102, saw block 502 may be removed.

Figure 6:
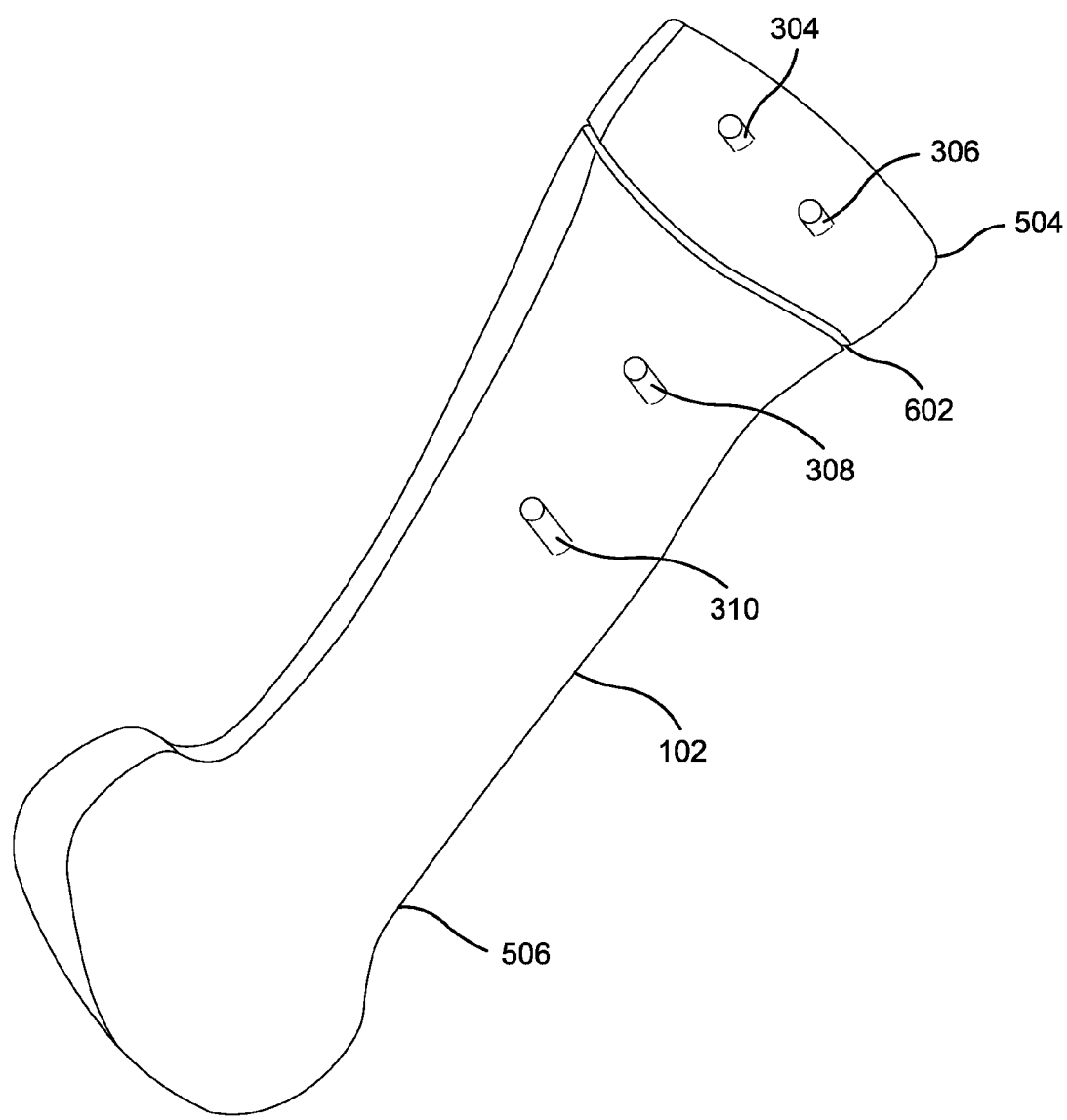
FIG. 6 illustrates a perspective view of the metatarsal bone after a saw cut has been made, in accordance with an embodiment.

FIG. 6 illustrates a perspective view of the metatarsal bone after a saw cut has been made, in accordance with an embodiment. The cut line 602 shown in FIG. 6 shows the cut made completely through metatarsal bone 102 using saw block 502. As a result, metatarsal bone 102 is split into a first metatarsal bone segment 504 and a second metatarsal bone segment 506. First metatarsal bone segment 504 represents a proximal bone section and second metatarsal bone segment 506 represents a distal bone section. K-wire pins 304 and 306 reside on first metatarsal bone segment 504. K-wire pins 308 and 310 reside on second metatarsal bone segment 506.

Figure 7:
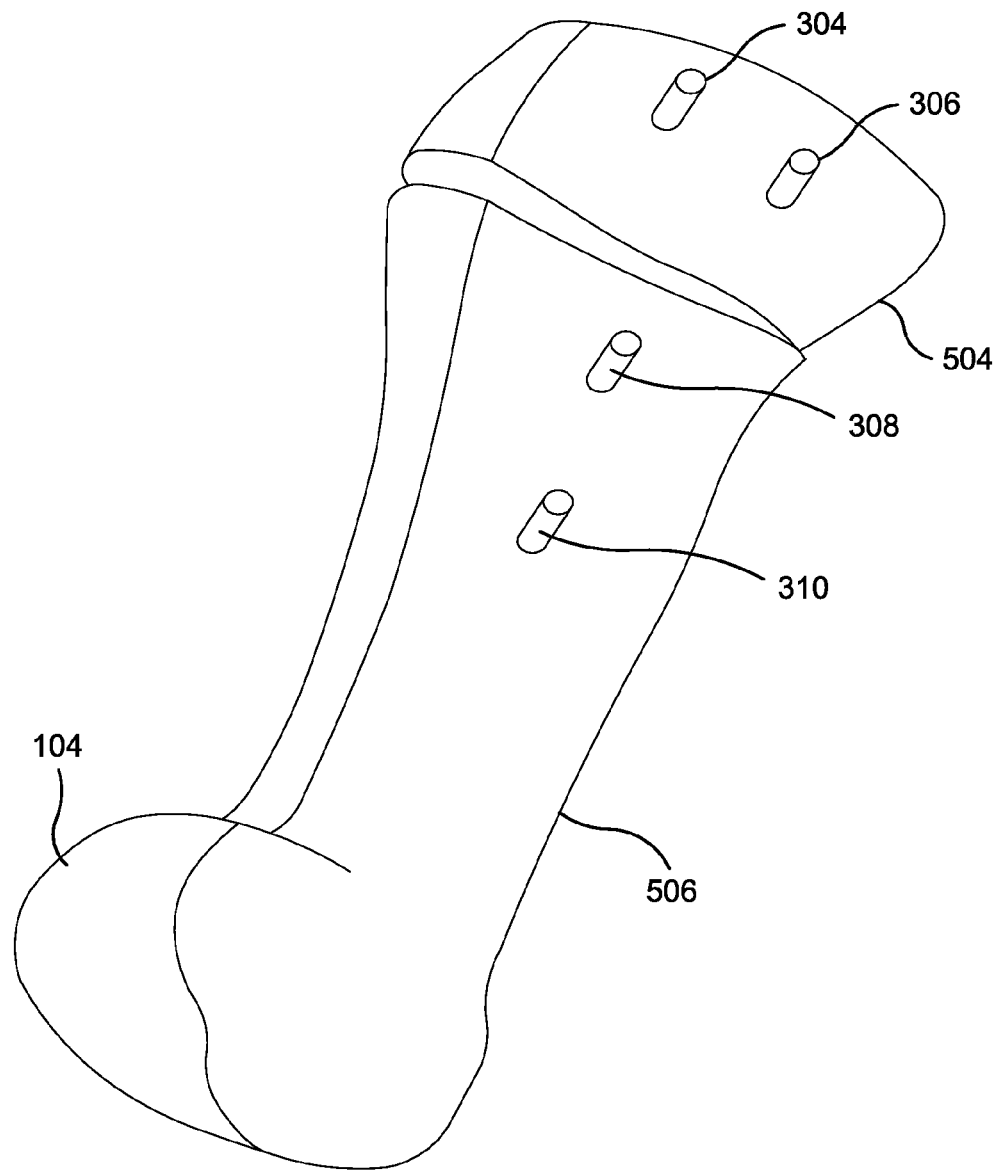
FIG. 7 illustrates a perspective view of the metatarsal bone with a corrective angle applied to the second metatarsal bone segment, in accordance with an embodiment.

FIG. 7 illustrates a perspective view of the metatarsal bone with a corrective angle applied to the second metatarsal bone segment, in accordance with an embodiment. Second metatarsal bone segment 506 has been oriented at a 5 degree corrective angle relative to first metatarsal bone segment 504 to ensure that bunion 104 no longer protrudes. While FIG. 7 illustrates a 5 degree corrective angle, any different degree corrective angle may also be used to orient second metatarsal bone segment 506 and first metatarsal bone segment 504 in accordance with the embodiments of the present invention described herein.

Figure 8:
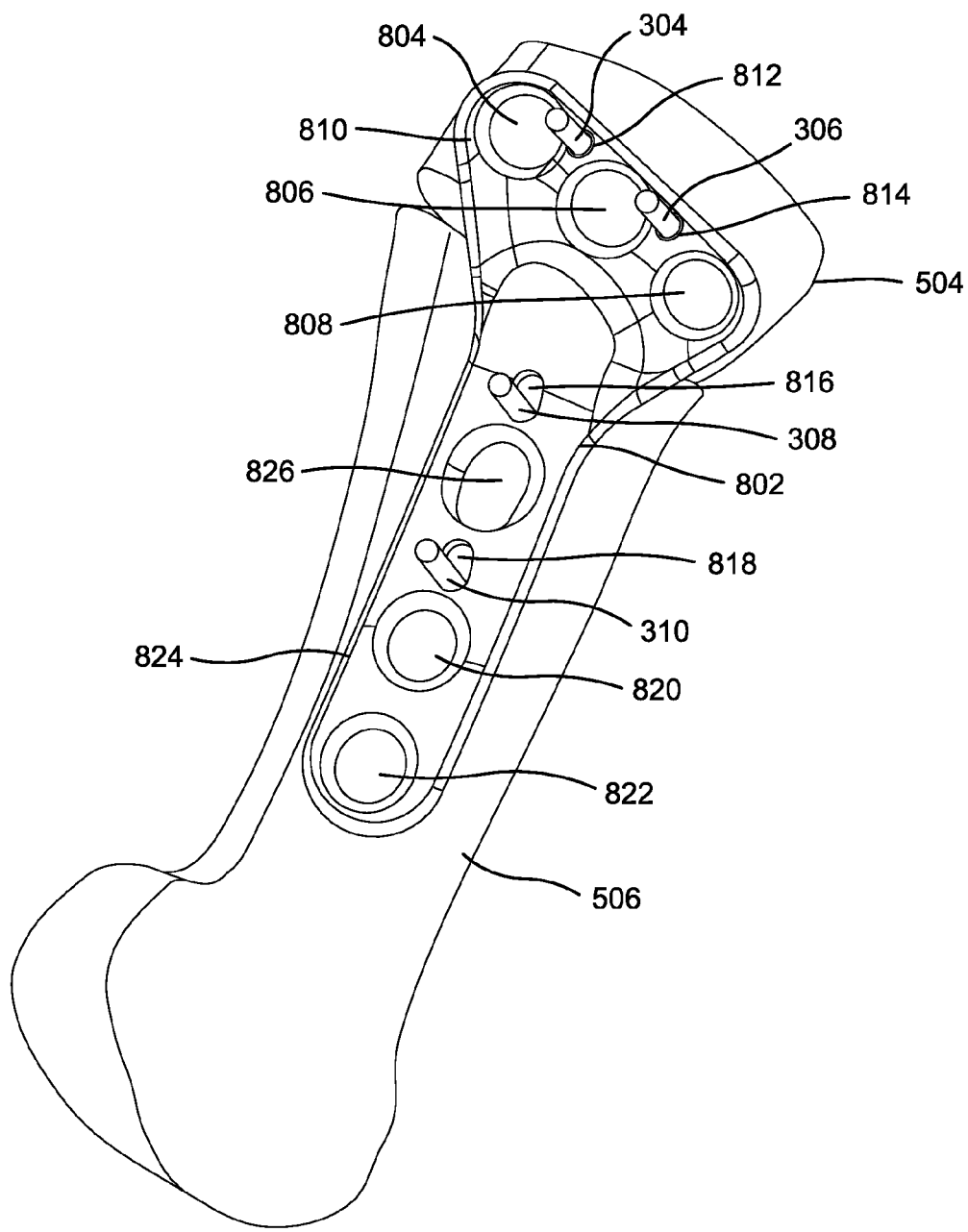
FIG. 8 illustrates a perspective view of a mating plate placed over the K-wire pins on the metatarsal bone, in accordance with an embodiment.

FIG. 8 illustrates a perspective view of a mating plate placed over the K-wire pins on the metatarsal bone, in accordance with an embodiment. Mating plate 802 is adapted to mate with K-wire pins 304, 306, 308, and 310 at pin holes 812, 814, 816, and 818, based on the 5 degree corrective angle between first metatarsal bone segment 504 and second metatarsal bone segment 506. Mating plate 802 includes guide holes 804, 806, and 808 on a proximal mating plate section 810 which corresponds to first metatarsal bone segment 504. Mating plate 802 further includes guide holes 820 and 822, along with a compression screw guide hole 826 on a distal mating plate section 824 which corresponds to second metatarsal bone segment 506. Pin holes 816 and 818 are enlarged relative to other pin holes to facilitate movement of the second metatarsal bone segment 506 and K-wire pins 308 and 310 with respect to the mating plate 802. Although not shown in FIG. 8, pilot holes may be drilled into the areas of guide holes 804, 806, and 808. The pilot holes are drilled so that metatarsal bone 102 and mating plate 802 can receive bone screws to affix mating plate 802 to metatarsal bone 102.

Figure 9:
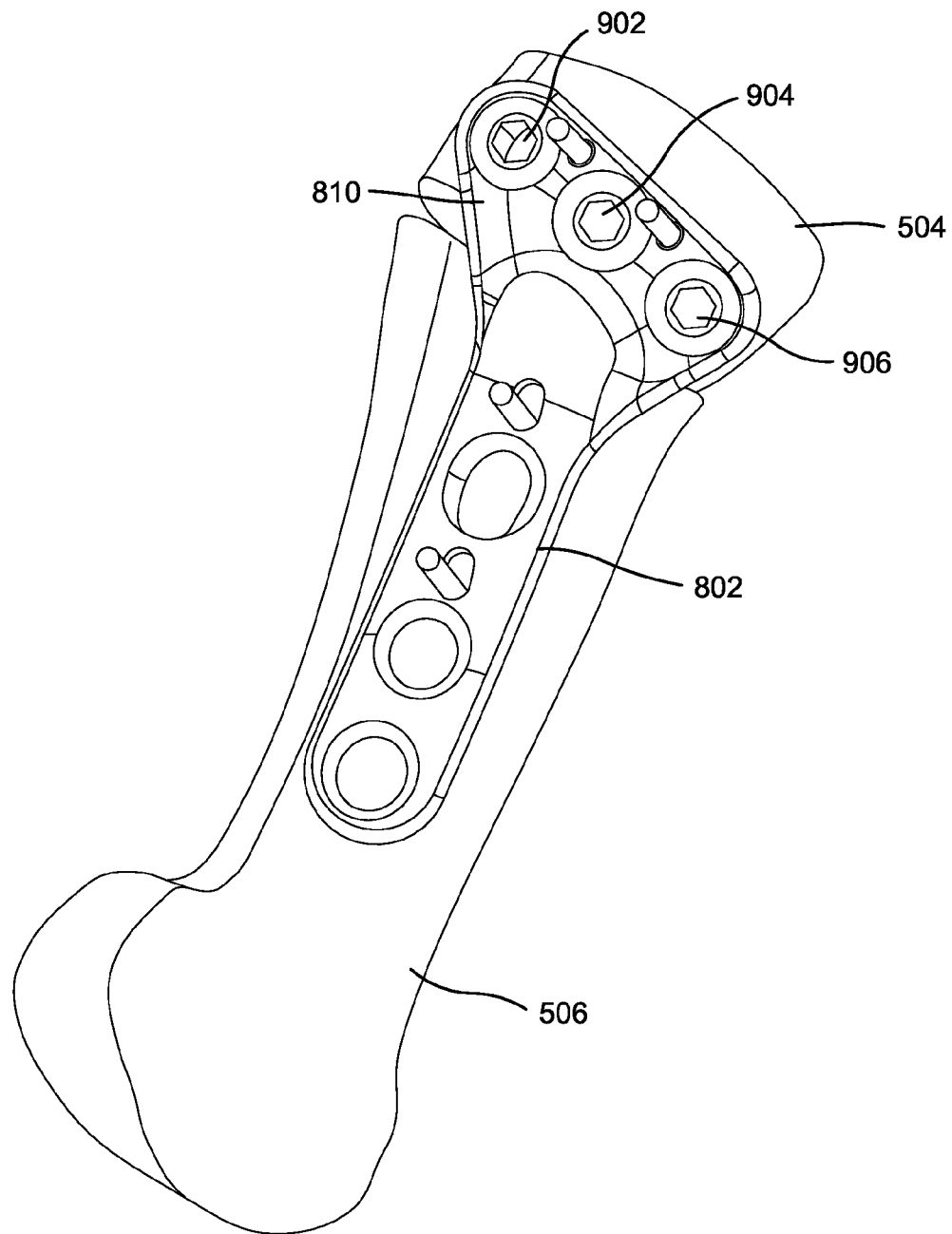
FIG. 9 illustrates a perspective view of mating plate affixed to the first metatarsal bone with bone screws, in accordance with an embodiment.

FIG. 9 illustrates a perspective view of mating plate 802 affixed to the first metatarsal bone with bone screws, in accordance with an embodiment. Three 3.5 mm bone screws 902, 904, and 906 are shown having been screwed into pilot holes drilled into the areas of guide holes 804, 806, and 808. As a result, proximal mating plate section 810 of mating plate 802 is attached and secured to first metatarsal bone segment 504.

Figure 10:
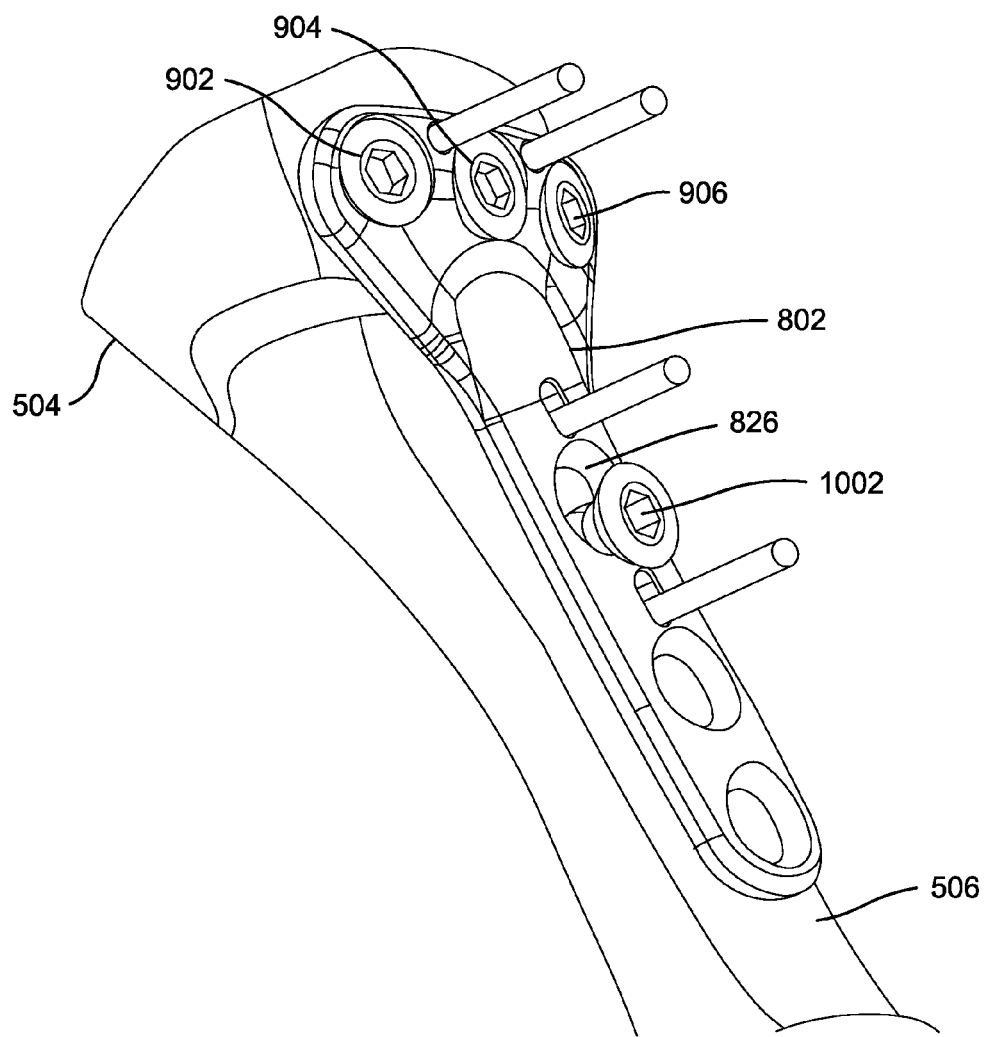
FIG. 10 illustrates a perspective view of the mating plate affixed to the first metatarsal bone segment and a compression screw applied to the area of the compression screw guide hole, in accordance with an embodiment.

FIG. 10 illustrates a perspective view of the mating plate affixed to the first metatarsal bone segment and a compression screw applied to the area of the compression screw guide hole, in accordance with an embodiment. A 3.5 mm bone screw or compression screw 1002 is screwed into to the area of compression screw guide hole 826 to affect compression across mating plate 802 and between second metatarsal bone segment 506 and first metatarsal bone segment 504. Before compression screw 1002 is screwed in, a pilot hole (not shown) is drilled into second metatarsal bone segment 506 at the area of compression screw guide hole 826.

Figure 11:
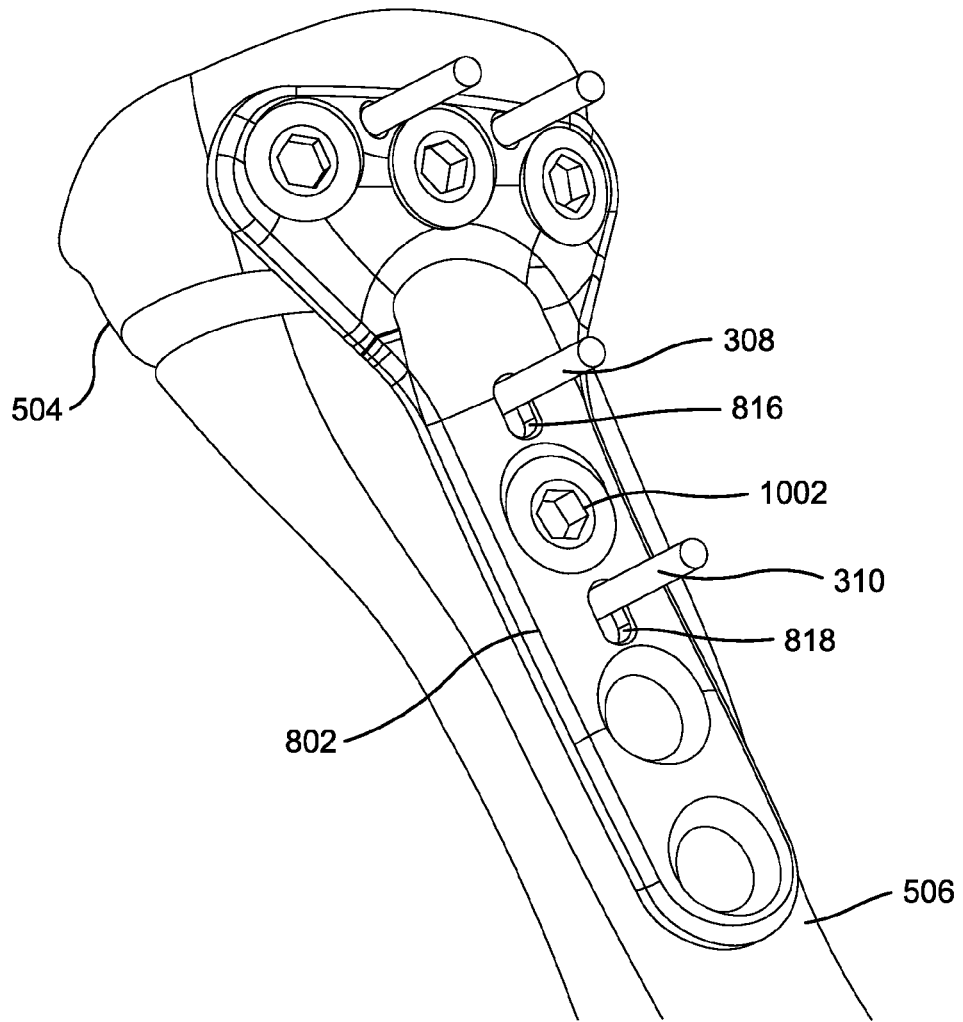
FIG. 11 illustrates a perspective view of the mating plate affixed to both the first metatarsal bone segment and the second metatarsal bone segment, in accordance with an embodiment.

FIG. 11 illustrates a perspective view of the mating plate affixed to both the first metatarsal bone segment and the second metatarsal bone segment, in accordance with an embodiment. As compression screw 1002 is secured in second metatarsal bone segment 506, this causes second metatarsal bone segment 506 to move in a proximal direction towards first metatarsal bone segment 504. K-wire pins 308 and 310 also move within pinholes 816 and 818 in a proximal direction towards first metatarsal bone segment 504.

Figure 12:
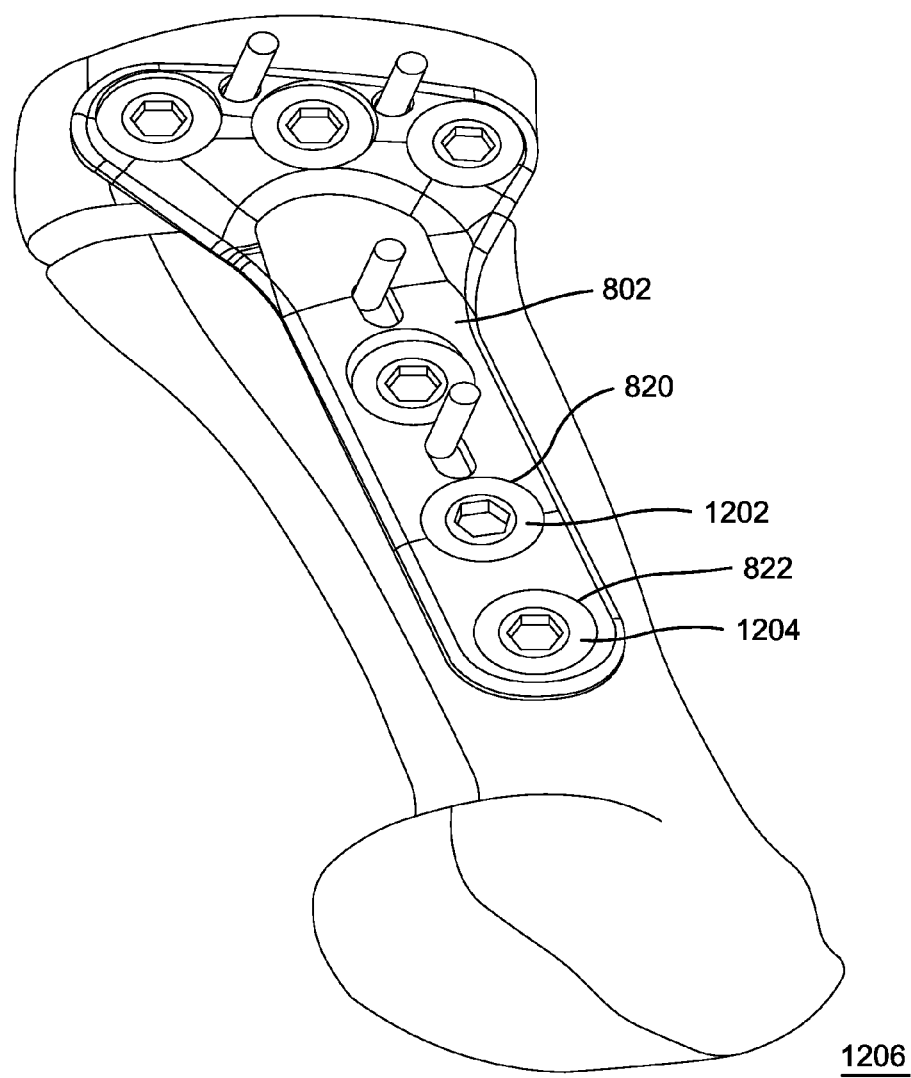
FIG. 12 illustrates a perspective view of the mating plate affixed to both the first metatarsal bone segment and the second metatarsal bone segment, in accordance with an embodiment.

FIG. 12 illustrates a perspective view of the mating plate affixed to both the first metatarsal bone segment and the second metatarsal bone segment, in accordance with an embodiment. Although not shown, two pilot holes are drilled into the areas of guide holes 820 and 822. Two bone screws 1202 and 1204 are screwed into second metatarsal bone segment 506 at the aforementioned pilot holes. After all bone screws are screwed into their corresponding pilot holes, the corrective construct 1206 representing a corrected metatarsal bone to remove the protrusion of the bunion is complete.

Figure 13:
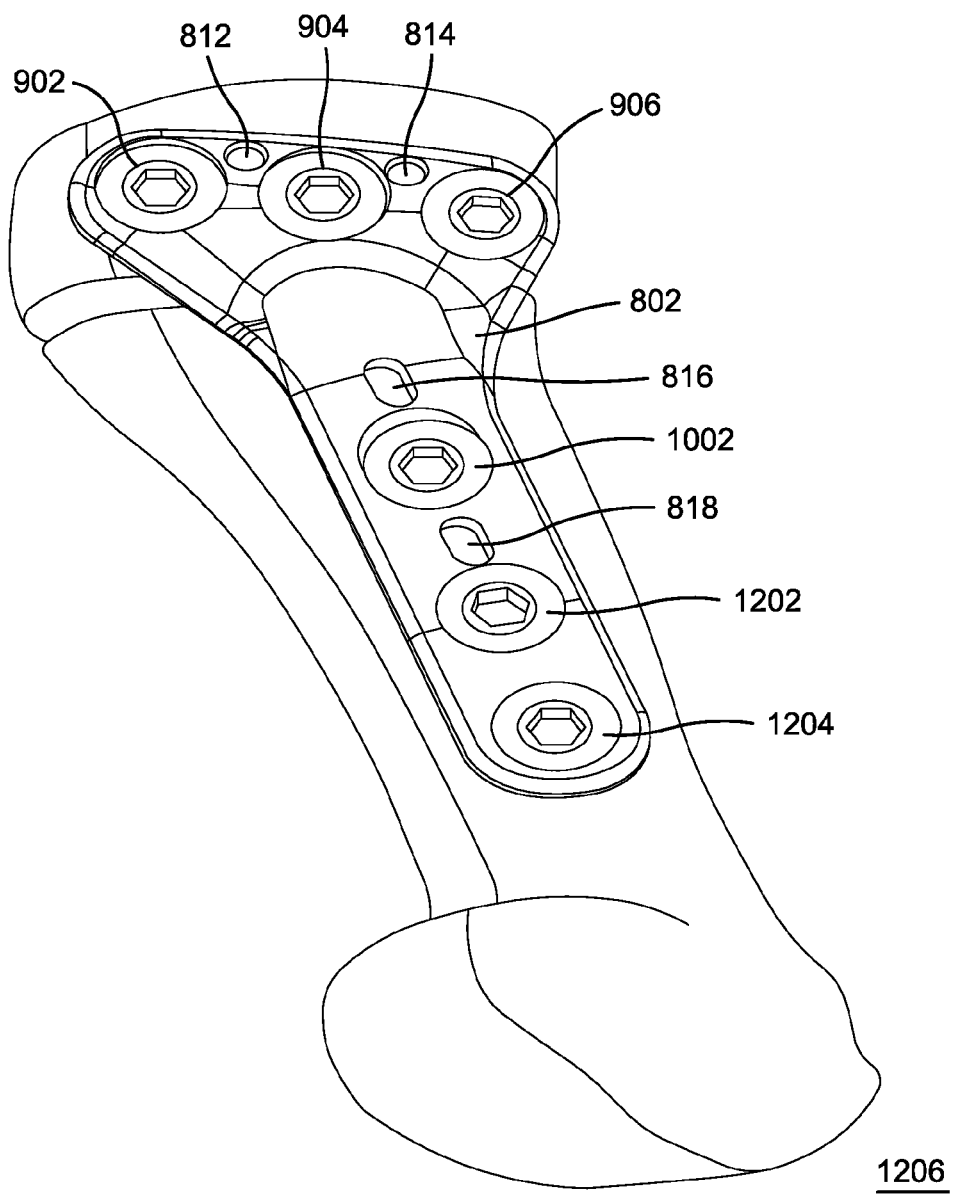
FIG. 13 illustrates a perspective view of the corrective construct after the K-wire pins are removed, in accordance with an embodiment.

FIG. 13 illustrates a perspective view of the corrective construct after the K-wire pins are removed, in accordance with an embodiment. K-wire pins 304, 306, 308, and 310 are removed from pin holes 812, 814, 816, and 818, after the procedure is completed prior to closure. Although FIGS. 1 through 13 have described a system and method for completing a bunionectomy surgery on a left foot metatarsal bone using a 5 degree corrective angle, it is understood that several mating plates corresponding to various corrective angles may be available to surgeons. Additionally, the mating plates may be either left mating plates for left feet or right mating plates for right feet.

Figure 14:
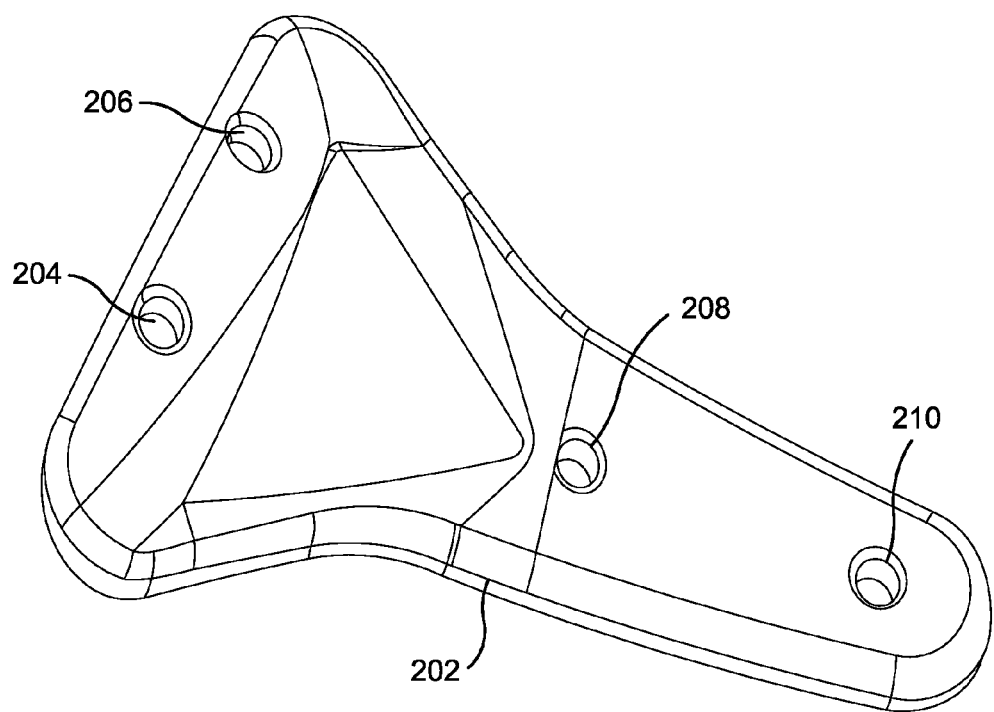
FIG. 14 illustrates a perspective view of a saw template, in accordance with an embodiment.

FIG. 14 illustrates a perspective view of a saw template, in accordance with an embodiment. Saw template 202 includes first, second, third, and fourth pin holes 204, 206, 208, and 210. Pin holes 204, 206, 208, and 210 of saw template 202 receive K-wire pins which are attached to a metatarsal bone.

Figure 15:
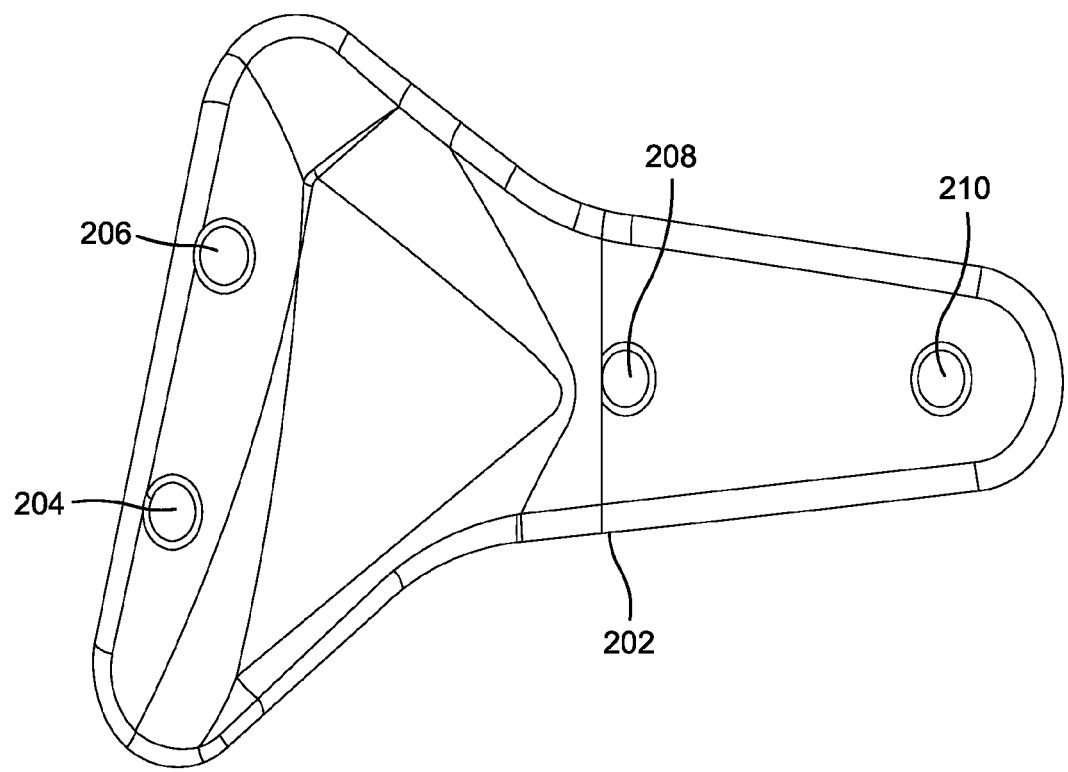
FIG. 15 illustrates a top view of the saw template, in accordance with an embodiment.

FIG. 15 illustrates a top view of the saw template, in accordance with an embodiment.

Figure 16:
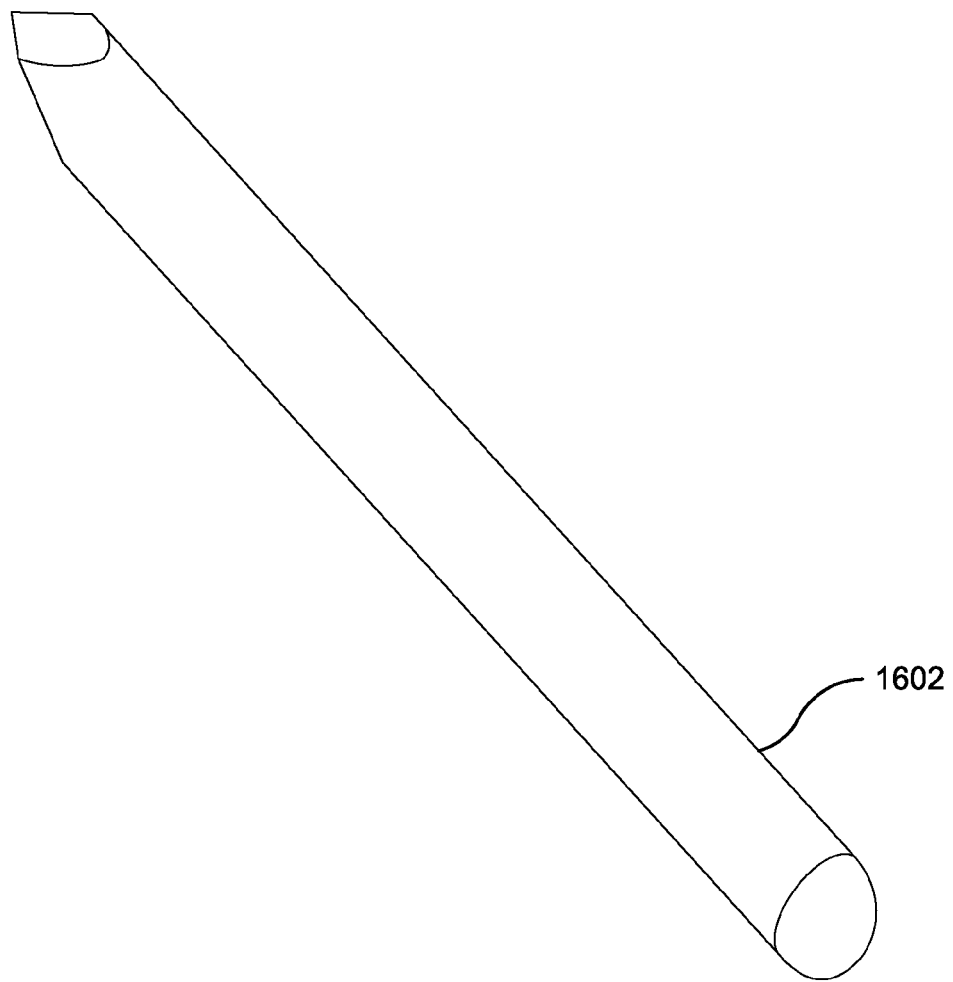
FIG. 16 illustrates a perspective view of a K-wire pin, in accordance with an embodiment.

FIG. 16 illustrates a perspective view of a K-wire pin, in accordance with an embodiment. K-wire pin 1602 as shown is a 1.5 mm k-wire pin, and 20 mm long.

Figure 17:
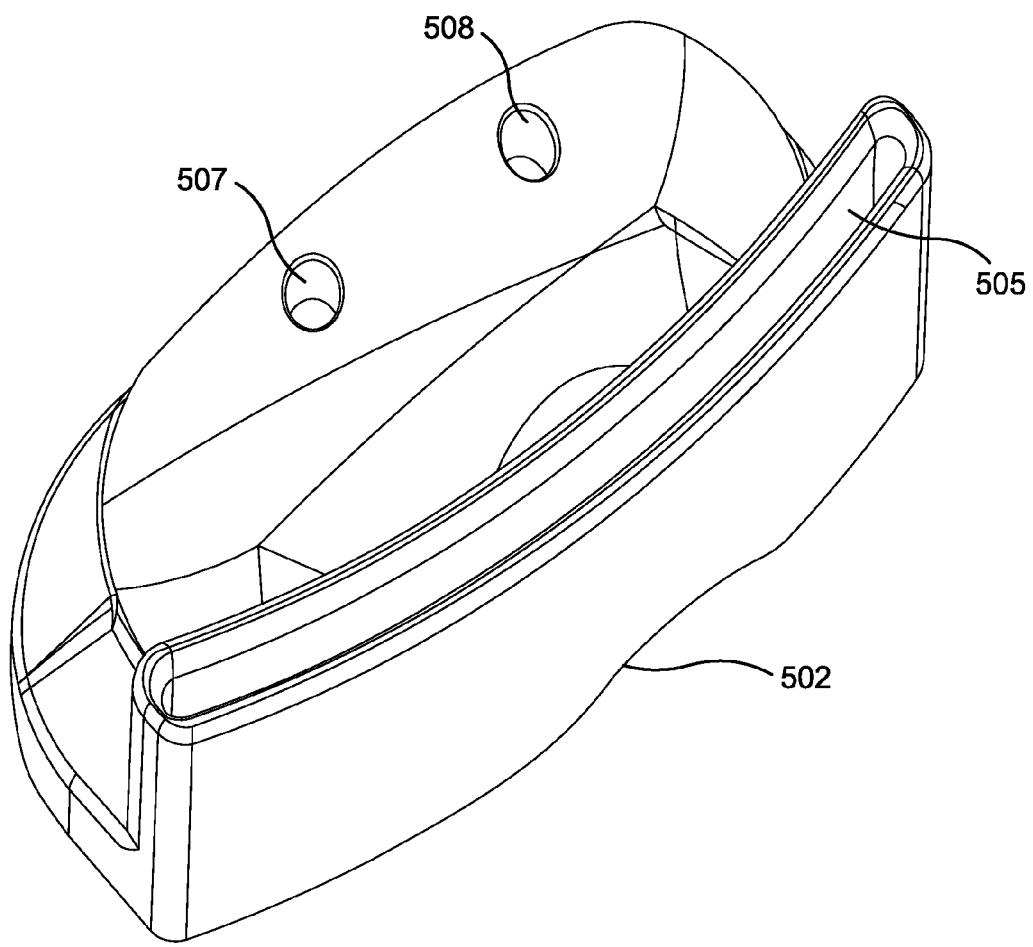
FIG. 17 illustrates a perspective view of a saw block with two pin holes and a saw slot in accordance with an embodiment.

FIG. 17 illustrates a perspective view of a saw block with two pin holes and a saw slot in accordance with an embodiment. Saw block 502 includes two pin holes 507 and 508 which may mate with two K-wire pins to facilitate attachment of saw block 502 to metatarsal bone 102. Saw slot 505 provides an opening thru which a saw may be inserted to cut along the saw slot 505. The curvature of saw slot 505 may be variable to receive an ideal saw blade for a particular procedure.

Figure 18:
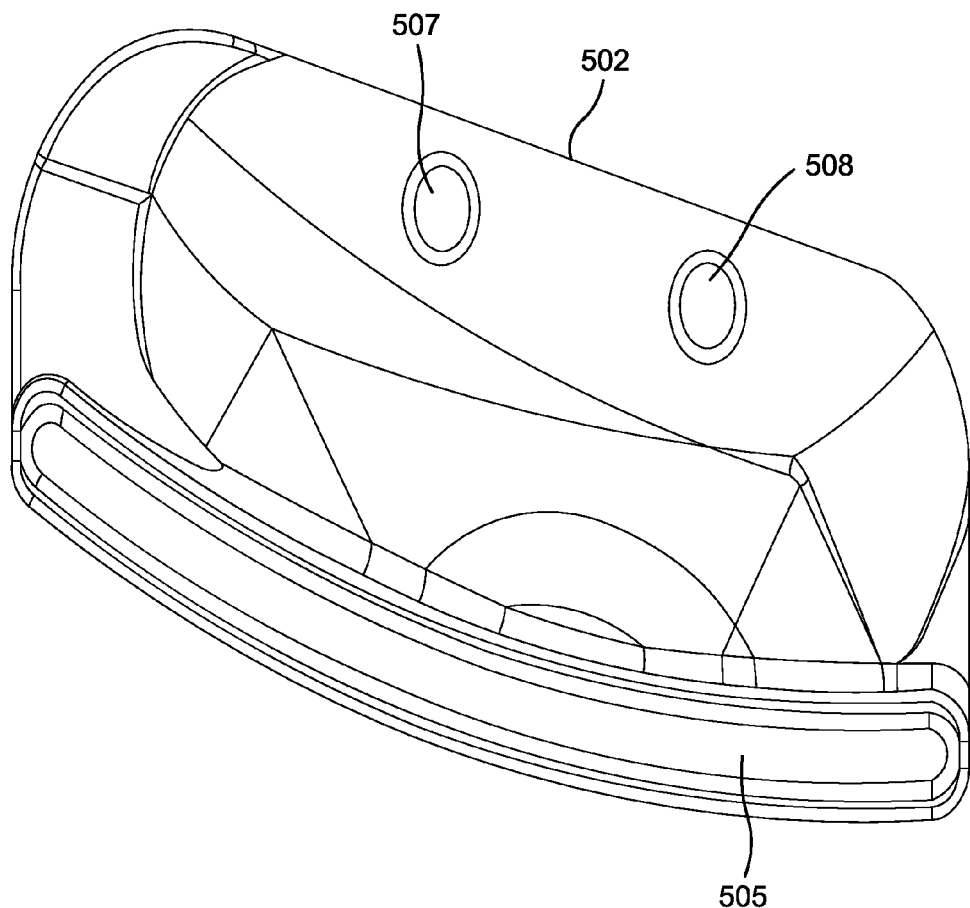
FIG. 18 illustrates a top view of the saw block, in accordance with an embodiment.

FIG. 18 illustrates a top view of the saw block, in accordance with an embodiment.

Figure 19:
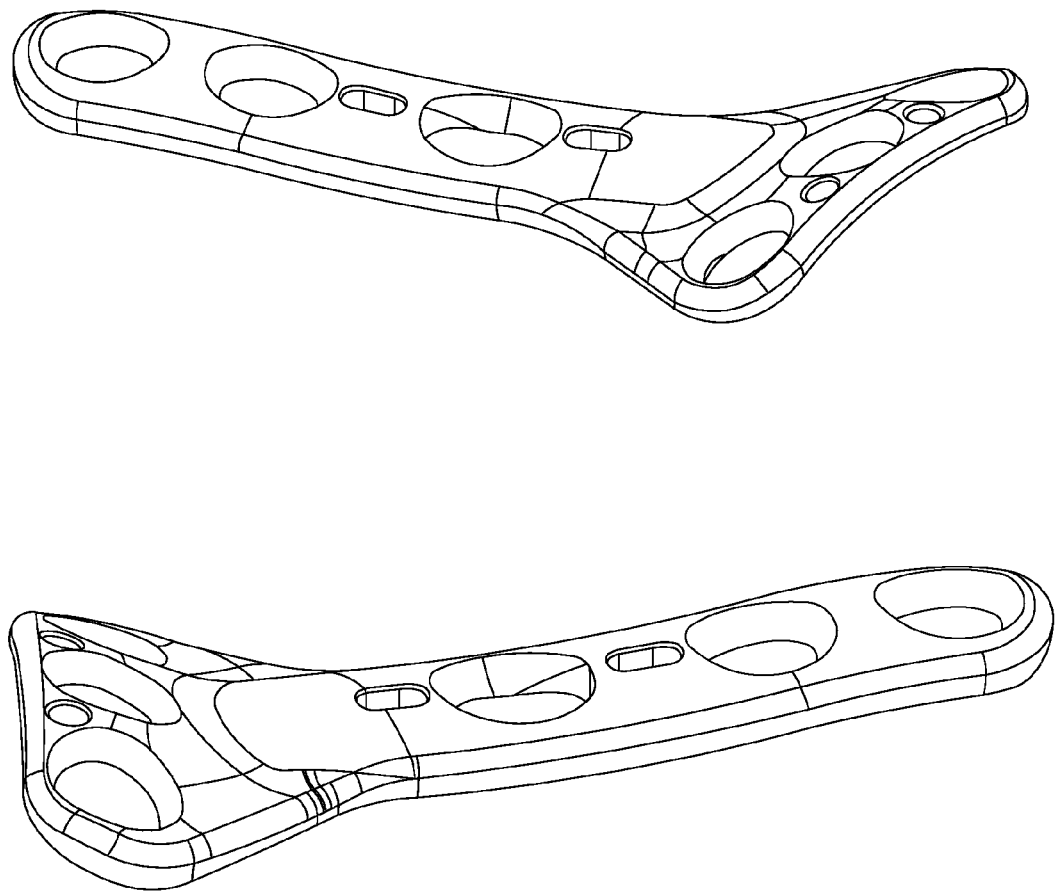
FIG. 19 illustrates a perspective view of a 5 degree bunionectomy plate or mating plate for the left foot from both a first perspective and a second perspective, in accordance with an embodiment.

FIG. 19 illustrates a perspective view of a 5 degree bunionectomy plate or mating plate for the left foot from both a first perspective and a second perspective, in accordance with an embodiment.

Figure 20:
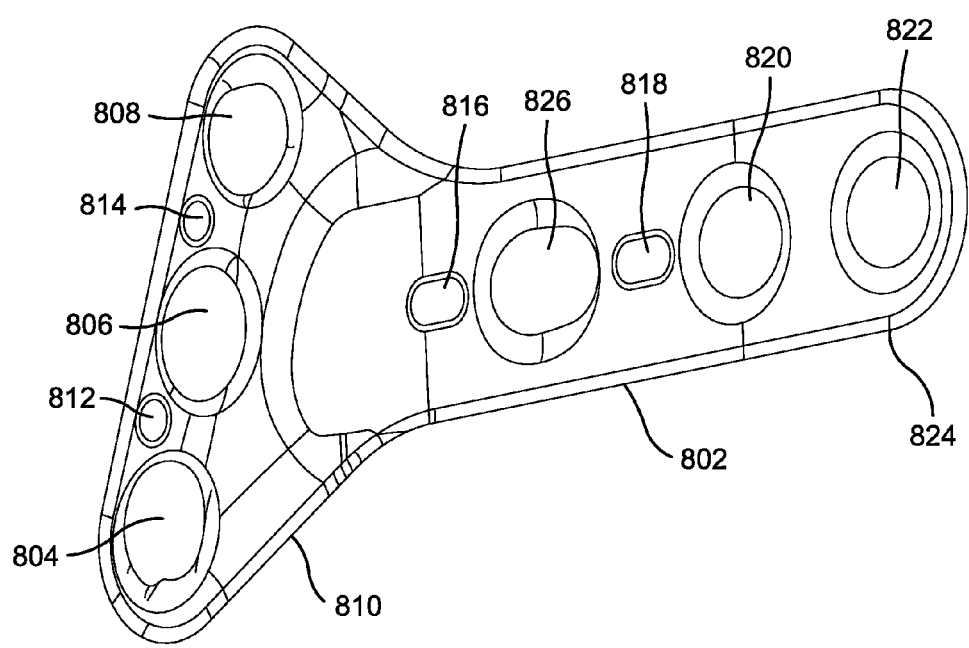
FIG. 20 illustrates a top view of a mating plate, in accordance with an embodiment.

FIG. 20 illustrates a top view of a mating plate, in accordance with an embodiment. Mating plate 802 is adapted to mate with K-wire pins at pin holes 812, 814, 816, and 818, to attach to first metatarsal bone segment 504 and second metatarsal bone segment 506. Mating plate 802 includes further includes guide holes 804, 806, and 808 on a proximal mating plate section 810 which connects to first metatarsal bone segment 504. Mating plate 802 further includes guide holes 820 and 822, along with a compression screw guide hole 826 on a distal mating plate section 824 which connects to second metatarsal bone segment 506. Pin holes 816 and 818 are enlarged relative to other pin holes to facilitate movement of mating plate 802 with respect to K-wire pins when a compression screw is screwed into the area of compression screw guide hole 826 causing second metatarsal bone segment 506 to move proximally towards first metatarsal bone segment 504. The aforementioned guide holes and compression screw guide hole are areas facilitating the insertion or screwing of bone screws.

Figure 21:
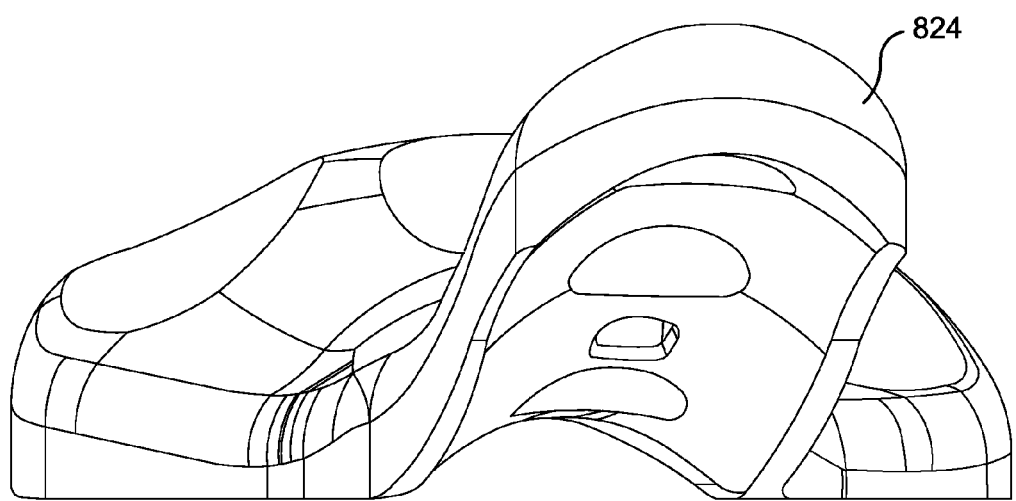
FIG. 21 illustrates a first side view of the mating plate where the front shows the distal mating plate section, in accordance with an embodiment.

FIG. 21 illustrates a first side view of the mating plate where the front shows the distal mating plate section, in accordance with an embodiment.

Figure 22:
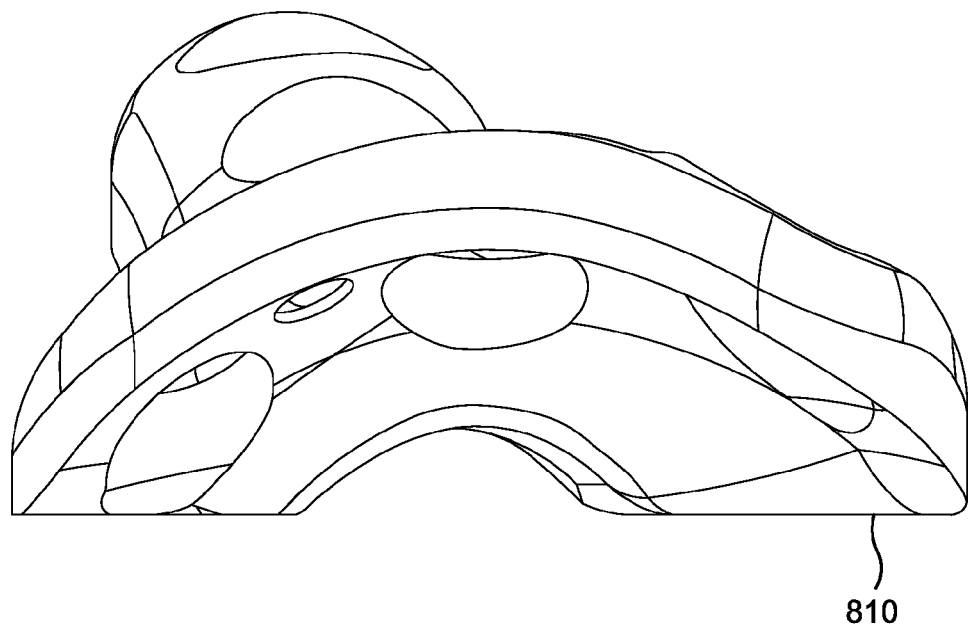
FIG. 22 illustrates a second side view of the mating plate where the front shows the proximal mating plate section, in accordance with an embodiment.

FIG. 22 illustrates a second side view of the mating plate where the front shows the proximal mating plate section, in accordance with an embodiment.

Figure 23:
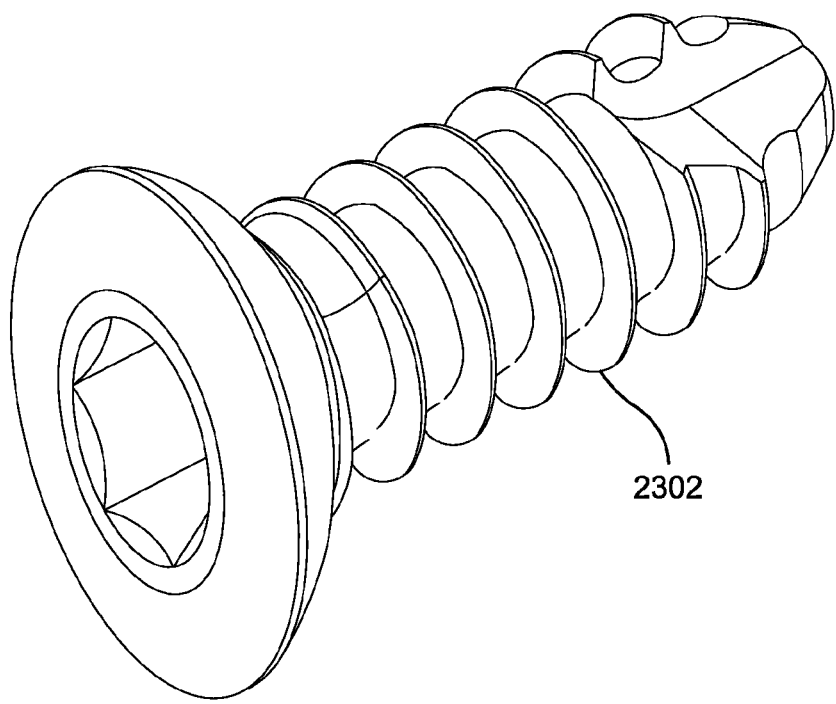
FIG. 23 illustrates a perspective view of a bone screw with an Allen hex head, in accordance with an embodiment.

FIG. 23 illustrates a perspective view of a bone screw with an Allen hex head, in accordance with an embodiment. Bone screw 2302 is a 3.5 mm×12 mm long bone screw, but the size and length can vary.

Figure 24:
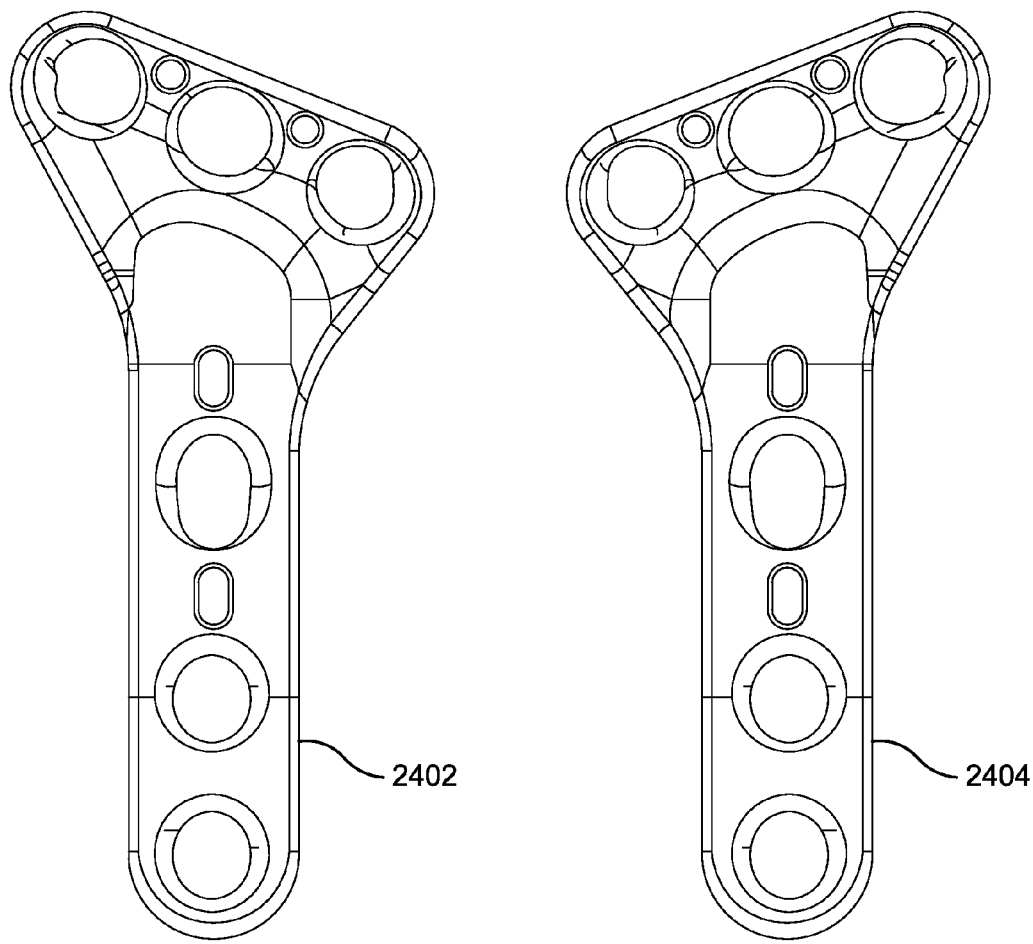
FIG. 24 illustrates a top view of medium sized mating plates, in accordance with an embodiment.

FIG. 24 illustrates a top view of medium sized mating plates, in accordance with an embodiment. Mating plate 2402 is designed for use with a left foot metatarsal bone and mating plate 2404 is designed for use with a right foot metatarsal bone.

Figure 25:
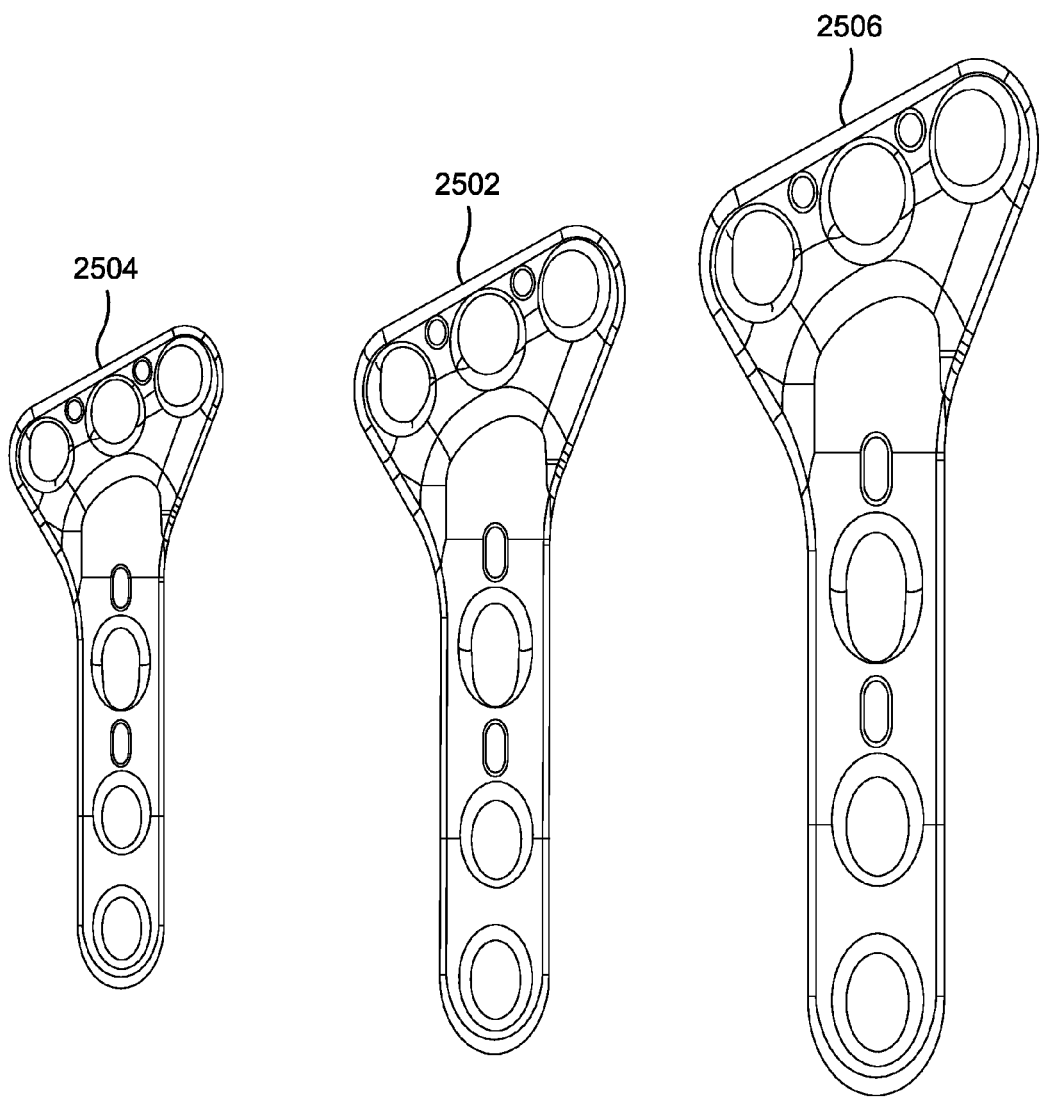
FIG. 25 illustrates a top down view of three sizes of mating plates, in accordance with an embodiment.

FIG. 25 illustrates a top down view of three sizes of mating plates, in accordance with an embodiment. Mating plate 2502 is a medium size or standard size. Mating plate 2504 is a small size, which is 20 percent smaller than the medium mating plate 2502. Mating plate 2506 is a large size, which is 20 percent larger than the medium mating plate 2502.

Figure 26:
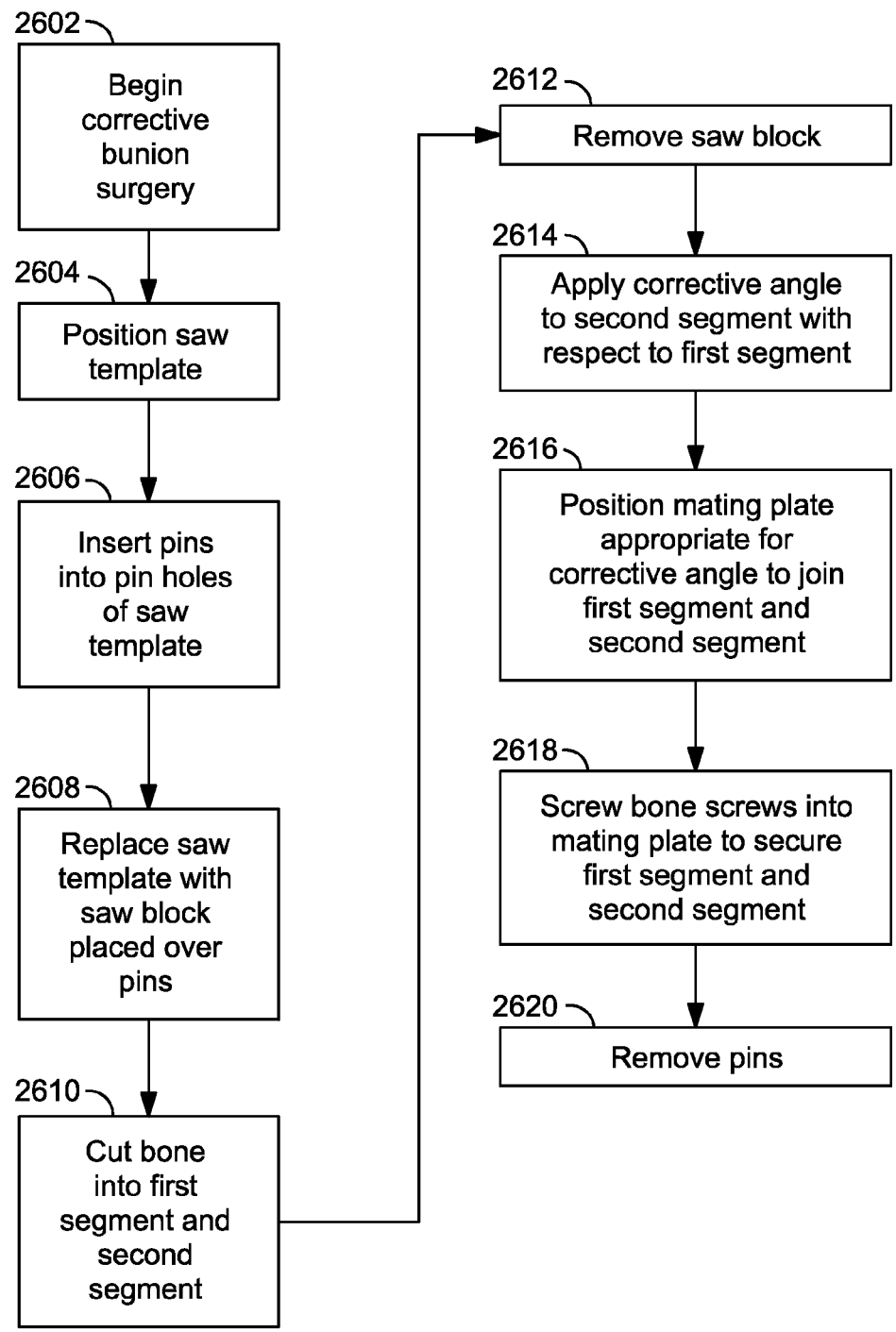
FIG. 26 illustrates a method for performing corrective bunionectomy surgery in accordance with an embodiment.

FIG. 26 illustrates a method for performing corrective bunionectomy surgery in accordance with an embodiment. At step 2602, corrective surgery on a bunion begins. At this point, a surgeon may operate on the foot of a patient, and expose the first metatarsal bone.

At step 2604, a saw template is positioned at a proximal portion of the metatarsal bone. The saw template has a plurality of pin holes. The saw template is placed to facilitate the placement of pins.

At step 2606, a plurality of pins is inserted into the plurality of pin holes of the saw template. The pins may be K-wire pins and the purpose of the pins is to first support a saw block which facilitates cutting of the metatarsal bone, and then support a mating plate to recombine the cut segments of the bone as a corrective construct representing a reconstructed metatarsal bone curing the protrusion of a bunion.

At step 2608, the saw template is replaced with a saw block placed over a portion of the plurality of pins. The saw block includes a saw slot which serves as a guideline for cutting. The saw block is placed onto two of the pins which reside at a proximal portion of the metatarsal bone, the two pins holding the saw block in place to facilitate cutting of the metatarsal bone into a first metatarsal bone segment and a second metatarsal bone segment.

At step 2610, the bone is cut into a first metatarsal bone segment and a second metatarsal bone segment based on the position of the saw block.

At step 2612, the saw block is removed.

At step 2614, a corrective angle is applied to the second metatarsal bone segment relative to the first metatarsal bone segment.

At step 2616, a mating plate appropriate for the corrective angle is positioned over the plurality of pins to join the first metatarsal bone segment and the second metatarsal bone segment.

At step 2618, bone screws are screwed into the mating plate to secure the first bone segment and the second bone segment to form a corrective construct. More specifically, pilot holes in the bone are made based on guide holes of the mating plate. Three bone screws are screwed into a proximal mating plate section of the mating plate to secure the mating plate to the first metatarsal bone segment. Then, a compression screw is screwed into a proximal guide hole on a distal mating plate section of the mating plate. Screwing the compression screw causes the second metatarsal bone segment to move proximally towards the first metatarsal bone segment. Two bone screws are screwed into the distal mating plate section to fully secure the second metatarsal bone segment to the mating plate.

At step 2620, the pins are removed to complete the corrective construct. Thus, the bunionectomy surgery is complete, and the corrected metatarsal bone will not have a bunion protrusion.

The foregoing Detailed Description is understood as being in every respect illustrative and exemplary, but not restrictive, and the scope of the invention disclosed herein is not to be determined from the Detailed Description, but rather from the claims as interpreted according to the full breadth permitted by the patent laws. It is understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A mating plate for joining a first bone segment and a second bone segment, comprising:
   a proximal mating plate section comprising:
      a plurality of pin holes for mating with a plurality of pins on the first bone segment; and
      a plurality of guide holes for receiving bone screws into the first bone segment; and
   a distal mating plate section comprising:
      a plurality of enlarged pin holes for mating with a plurality of pins on the second bone segment;
      a compression screw guide hole for receiving a compression bone screw into the second bone segment; and
      a plurality of guide holes for receiving bone screws into the second bone segment;
   wherein tightening of the compression bone screw causes the second bone segment to move in a proximal direction towards the first bone segment and the plurality of pins in the second bone segment to move only in a proximal direction within the enlarged pin holes toward the first bone segment.

2. The mating plate of claim 1, wherein the proximal mating plate section is angled relative to the distal mating plate section.

3. The mating plate of claim 2, wherein the proximal mating plate section is angled approximately 5 degrees with respect to the distal mating plate section.

4. The mating plate of claim 1, wherein the distal mating plate section is angled relative to the proximal mating plate section.

5. The mating plate of claim 4, wherein the distal mating plate section is angled approximately 5 degrees with respect to the proximal mating plate section.

6. The mating plate of claim 1, further comprising:
   a top surface; and
   a bottom surface opposite the top surface.

7. The mating plate of claim 6, wherein the top surface and the bottom surface of the proximal mating plate section are curved between a medial side and a lateral side of the mating plate.

8. The mating plate of claim 6, wherein the top surface and the bottom surface of the distal mating plate section are curved along a medial-lateral axis of the mating plate.

9. The mating plate of claim 6, wherein the bottom surface of the mating plate is configured to mate with the first bone segment and the second bone segment.

10. The mating plate of claim 1, wherein the proximal mating plate section is coupled to the distal mating plate section at an engagement section.

11. The mating plate of claim 10, wherein the proximal mating plate section is angled relative to the distal mating plate section at the engagement section.

12. The mating plate of claim 1, wherein the proximal mating plate section is angled relative to a longitudinal axis of the mating plate in a direction for a left foot metatarsal bone.

13. The mating plate of claim 1, wherein the proximal mating plate section is angled relative to a longitudinal axis of the mating plate in a direction for a right foot metatarsal bone.

14. The mating plate of claim 1, wherein the proximal mating plate section is configured to contact the first bone segment, wherein the first bone segment is an end of a bone.

15. The mating plate of claim 1, wherein the distal mating plate section is configured to align with a long axis of a bone.

16. The mating plate of claim 1, wherein the plurality of guide holes in the proximal mating plate section comprises at least one of two and three guide holes.

17. The mating plate of claim 16, wherein the plurality of pin holes in the proximal mating plate section comprises at least one of one and two pin holes.

18. The mating plate of claim 17, wherein each of the pin holes is positioned between the guide holes.

19. The mating plate of claim 1, wherein the plurality of guide holes in the distal mating plate section comprises at least one and two guide holes.

20. The mating plate of claim 1, wherein the plurality of enlarged pin holes in the distal mating plate section comprises at least one and two enlarged pin holes.

21. The mating plate of claim 20, wherein the plurality of enlarged pin holes are positioned adjacent the compression screw guide hole.

22. The mating plate of claim 21, wherein the plurality of enlarged pin holes and the compression screw guide hole are positioned proximal to the plurality of guide holes in the distal mating plate section.

23. The mating plate of claim 1, wherein the first bone segment and the second bone segment are extremity bones.

24. The mating plate of claim 1, wherein the plurality of enlarged pin holes are sized to guide the plurality of pins in a direction toward the first bone segment.

25. A mating plate system for joining a first bone segment and a second bone segment, comprising:
  a plurality of pins, comprising:
    a first set of pins; and
    a second set of pins; and
  a mating plate, comprising:
    a proximal mating plate section comprising:
      a plurality of pin holes for mating with the first set of pins inserted into the first bone segment; and
      a plurality of guide holes for receiving bone screws into the first bone segment; and
    a distal mating plate section comprising:
      a plurality of enlarged slots for mating with the second set of pins inserted into the second bone segment;
      a compression screw guide hole for receiving a compression bone screw into the second bone segment; and
      a plurality of guide holes for receiving bone screws into the second bone segment;
    wherein tightening of the compression bone screw causes the second bone segment to move in a proximal direction towards the first bone segment and the second set of pins to move only in a proximal direction towards the first bone segment.

26. The mating plate system of claim 25, wherein the plurality of enlarged slots are positioned adjacent the compression screw guide hole.

27. The mating plate system of claim 26, wherein the plurality of enlarged slots and the compression screw guide hole are positioned proximal to the plurality of guide holes in the distal mating plate section.

28. The mating plate system of claim 25, wherein the first bone segment and the second bone segment are extremity bones.

29. The mating plate system of claim 25, wherein the plurality of enlarged slots are sized to guide the plurality of pins in a direction toward the first bone segment.

30. The mating plate system of claim 25, wherein the plurality of pins are non-threaded.

31. The mating plate system of claim 23, wherein the extremity bones are selected from bones of the hands and feet.

* * * * *